(12) United States Patent
Naughton et al.

(10) Patent No.: US 9,458,486 B2
(45) Date of Patent: *Oct. 4, 2016

(54) CONDITIONED CELL CULTURE MEDIUM COMPOSITIONS AND METHODS OF USE

(71) Applicant: Allergan, Inc., Irvine, CA (US)

(72) Inventors: Gail K. Naughton, Del Mar, CA (US); David L. Horwitz, San Diego, CA (US); Mark Applegate, San Diego, CA (US); Joan Zeltinger, Encinitas, CA (US); Jonathan Mansbridge, La Jolla, CA (US); Andreas Kern, San Diego, CA (US); Lee K. Landeen, San Diego, CA (US); Anthony Ratcliffe, Del Mar, CA (US); R. Emmett Pinney, Poway, CA (US)

(73) Assignee: Allergen, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/842,129

(22) Filed: Mar. 15, 2013

(65) Prior Publication Data

US 2013/0209398 A1 Aug. 15, 2013

Related U.S. Application Data

(60) Continuation of application No. 13/417,017, filed on Mar. 9, 2012, which is a continuation of application No. 12/349,451, filed on Jan. 6, 2009, now Pat. No. 8,138,147, which is a division of application No. 11/538,380, filed on Oct. 3, 2006, now Pat. No. 8,361,485, which is a division of application No. 09/979,813, filed as application No. PCT/US00/13016 on May 12, 2000, now Pat. No. 7,118,746, which is a continuation-in-part of application No. 09/313,538, filed on May 14, 1999, now Pat. No. 6,372,494.

(51) Int. Cl.

| | |
|---|---|
| C12P 21/00 | (2006.01) |
| A61K 38/18 | (2006.01) |
| A61K 45/06 | (2006.01) |
| A61K 35/36 | (2015.01) |
| A61K 35/33 | (2015.01) |
| A61K 8/65 | (2006.01) |
| A61Q 19/08 | (2006.01) |
| C12N 5/073 | (2010.01) |
| A23L 1/30 | (2006.01) |
| A61K 8/02 | (2006.01) |
| A61K 8/64 | (2006.01) |
| A61Q 7/00 | (2006.01) |
| A61Q 19/00 | (2006.01) |
| C12N 5/071 | (2010.01) |
| A61K 38/39 | (2006.01) |
| A61K 35/35 | (2015.01) |
| C12N 5/077 | (2010.01) |
| C12N 5/0735 | (2010.01) |

(52) U.S. Cl.
CPC ............... *C12P 21/00* (2013.01); *A23L 1/30* (2013.01); *A61K 8/02* (2013.01); *A61K 8/0208* (2013.01); *A61K 8/64* (2013.01); *A61K 8/65* (2013.01); *A61K 35/33* (2013.01); *A61K 35/35* (2013.01); *A61K 35/36* (2013.01); *A61K 38/18* (2013.01); *A61K 38/1825* (2013.01); *A61K 38/39* (2013.01); *A61K 45/06* (2013.01); *A61Q 7/00* (2013.01); *A61Q 19/00* (2013.01); *A61Q 19/08* (2013.01); *C12N 5/0603* (2013.01); *C12N 5/0606* (2013.01); *C12N 5/069* (2013.01); *C12N 5/0629* (2013.01); *C12N 5/0656* (2013.01); *A61K 2800/86* (2013.01); *C12N 2502/1323* (2013.01)

(58) Field of Classification Search
CPC .. A61K 38/1825; A61K 38/18; A61K 35/36; A61K 38/39; A61K 35/33; A61K 8/65; A61K 45/06; C12N 5/0603; C12N 21/00; C12P 21/00; A61Q 19/00; A61Q 19/08
See application file for complete search history.

(56) References Cited

U.S. PATENT DOCUMENTS

| 4,458,678 A | 7/1984 | Yannas et al. |
| 4,485,096 A | 11/1984 | Bell et al. |

(Continued)

FOREIGN PATENT DOCUMENTS

| AU | 772829 | 5/2005 |
| AU | 20022345603 | 1/2007 |

(Continued)

OTHER PUBLICATIONS

Aaronson and Todaro, 1968, Virology 36, 254-261.*

(Continued)

*Primary Examiner* — Daniel C Gamett
(74) *Attorney, Agent, or Firm* — Laura L. Wine; Debra D. Condino

(57) ABSTRACT

Novel products comprising conditioned cell culture medium compositions and methods of use are described. The conditioned cell medium compositions of the invention may be comprised of any known defined or undefined medium and may be conditioned using any eukaryotic cell type. Once the cell medium of the invention is conditioned, it may be used in any state. Physical embodiments of the conditioned medium include, but are not limited to, liquid or solid, frozen, lyophilized or dried into a powder. Additionally, the medium is formulated with a pharmaceutically acceptable carrier as a vehicle for internal administration, applied directly to a food item or product, or formulated with a salve or ointment for topical applications. Also, the medium may be further processed to concentrate or reduce one or more factors or components contained within the medium.

7 Claims, 5 Drawing Sheets

(56) References Cited

U.S. PATENT DOCUMENTS

| | | | |
|---|---|---|---|
| 4,757,017 A | 7/1988 | Cheung | |
| 4,861,714 A | 8/1989 | Dean, Jr. et al. | |
| 4,885,163 A * | 12/1989 | Shaar et al. | 514/8.5 |
| 4,911,720 A | 3/1990 | Collier | |
| 4,963,489 A | 10/1990 | Naughton et al. | |
| 5,008,240 A | 4/1991 | Bentz et al. | |
| 5,032,508 A | 7/1991 | Naughton et al. | |
| 5,043,156 A | 8/1991 | Matsumoto et al. | |
| 5,053,230 A * | 10/1991 | Gazzani | 424/582 |
| 5,091,173 A | 2/1992 | Buultjens et al. | |
| 5,229,493 A | 7/1993 | Folkman et al. | |
| 5,266,480 A | 11/1993 | Naughton et al. | |
| 5,292,655 A * | 3/1994 | Wille, Jr. | 435/384 |
| 5,443,950 A | 8/1995 | Naughton et al. | |
| 5,460,939 A | 10/1995 | Hansbrough et al. | |
| 5,474,931 A | 12/1995 | DiSorbo et al. | |
| 5,478,560 A * | 12/1995 | Tominaga | A61K 8/44 424/401 |
| 5,478,739 A | 12/1995 | Slivka et al. | |
| 5,516,532 A | 5/1996 | Atala et al. | |
| 5,516,681 A | 5/1996 | Naughton et al. | |
| 5,565,347 A | 10/1996 | Fillatti et al. | |
| 5,618,544 A | 4/1997 | Brown | |
| 5,654,381 A | 8/1997 | Hrkach et al. | |
| 5,665,870 A * | 9/1997 | Rubin et al. | 530/412 |
| 5,667,791 A * | 9/1997 | Hersh et al. | 424/401 |
| 5,681,748 A | 10/1997 | DiSorbo et al. | |
| 5,693,625 A * | 12/1997 | Barritault et al. | 514/59 |
| 5,709,854 A | 1/1998 | Griffith-Cima | |
| 5,736,372 A | 4/1998 | Vacanti et al. | |
| 5,759,830 A | 6/1998 | Vacanti et al. | |
| 5,763,267 A | 6/1998 | Kurjan et al. | |
| 5,770,193 A | 6/1998 | Vacanti et al. | |
| 5,770,448 A | 6/1998 | Jones et al. | |
| 5,785,964 A | 7/1998 | Naughton et al. | |
| 5,830,708 A | 11/1998 | Naughton | |
| 5,843,766 A | 12/1998 | Applegate et al. | |
| 5,855,918 A | 1/1999 | Mrsny et al. | |
| 5,888,551 A | 3/1999 | Jimenez et al. | |
| 5,900,245 A | 5/1999 | Sawhney et al. | |
| 5,902,741 A | 5/1999 | Purchio et al. | |
| 5,935,849 A | 8/1999 | Schinstine et al. | |
| 5,965,125 A | 10/1999 | Mineau-Hanschke | |
| 6,080,724 A | 6/2000 | Chassaing et al. | |
| 6,132,717 A | 10/2000 | Schacht et al. | |
| 6,291,240 B1 | 9/2001 | Mansbridge | |
| 6,372,494 B1 | 4/2002 | Naughton | |
| 7,118,746 B1 | 10/2006 | Naughton et al. | |
| 7,160,726 B2 | 1/2007 | Mansbridge | |
| 7,196,054 B1 | 3/2007 | Drohan | |
| 8,138,147 B2 | 3/2012 | Naughton et al. | |
| 2004/0142861 A1 | 7/2004 | Mansbridge | |
| 2007/0077232 A1 | 4/2007 | Naughton et al. | |
| 2007/0218549 A1 | 9/2007 | Mansbridge | |
| 2007/0243158 A1* | 10/2007 | Ronfard | A61K 8/99 424/85.1 |

FOREIGN PATENT DOCUMENTS

| | | |
|---|---|---|
| CA | 1340222 | 12/1998 |
| CN | 1198628 C | 4/2005 |
| EP | 0175286 | 3/1986 |
| EP | 0358506 | 3/1990 |
| EP | 0476983 | 9/1991 |
| EP | 1178812 B2 | 12/2005 |
| JP | 6133124 | 2/1986 |
| JP | 61-108386 | 5/1986 |
| JP | 62-53927 | 3/1987 |
| JP | 62-249926 | 10/1987 |
| JP | 2004-534049 A | 11/2004 |
| NZ | 515476 | 5/2000 |
| RU | 2054924 | 2/1996 |
| RU | 2063743 | 7/1996 |
| RU | 2123837 | 12/1998 |
| RU | 2141814 | 11/1999 |
| RU | 2142783 | 12/1999 |
| RU | 2280459 | 7/2006 |
| SG | 106171 | 6/2006 |
| WO | WO-89-11529 | 11/1989 |
| WO | WO-91-16010 | 10/1991 |
| WO | 93/04164 A1 | 3/1993 |
| WO | WO-93-04164 | 3/1993 |
| WO | WO-93-17669 | 9/1993 |
| WO | WO-94-20133 | 9/1994 |
| WO | WO-94-25080 | 11/1994 |
| WO | WO-95-33821 A1 | 12/1995 |
| WO | WO-96-18726 | 6/1996 |
| WO | WO-96-39101 | 12/1996 |
| WO | WO-96-40174 | 12/1996 |
| WO | WO-96-40175 A1 | 12/1996 |
| WO | WO-97-21442 | 6/1997 |
| WO | WO-97-38777 A1 | 10/1997 |
| WO | WO-98-07832 | 2/1998 |
| WO | WO-98-16642 | 4/1998 |
| WO | WO-98-21312 | 5/1998 |
| WO | WO-98-30225 | 7/1998 |
| WO | WO-98-52543 | 11/1998 |
| WO | WO-99-11809 | 3/1999 |
| WO | WO-99-59615 | 11/1999 |
| WO | WO-00-29427 A2 | 5/2000 |
| WO | WO-00-46349 | 8/2000 |
| WO | WO-00-69449 A2 | 11/2000 |
| WO | WO-01-14527 A1 | 3/2001 |
| ZA | 2001/9381 | 1/2003 |

OTHER PUBLICATIONS

Scott and Das, Life Sciences 53:765-774 (1993).*
Sterling et al. Cancer Res. 42:3502-3506 (1982).*
JP2000-617908 Office Action mailed Nov. 2, 2011.
United States District Court, So. District of California. Case No. 3:09-cv-00122-JLS-NLS, Document 150, filed May 24, 2011, 30 pages.
United States District Court, So. District of California. Case No. 3:09-cv-00122-JLS-NLS, Document 228, filed Nov. 21, 2011, 14 pages.
O'Donnell-Tormey et al., "Secretion of Pyruvate. An Antioxidant Defense of Mammalian Cells," J Exp Med 165:500-514 (1987).
Szuro-Sudol and Nathan, "Suppression of Macrophage Oxidative Metabolism by Products of Malignant and Nonmalignant Cells," J Exp Med 156:945-961 (1982).
Grinnell, F., "Mini-Review on the Cellular Mechanisms of Disease: Fibroblasts, Myofibroblasts, and Wound Contraction," J Cell Biol 124:401-404 (1994).
Mio et al., "Human bronchial epithelial cells modulate collagen gel contraction by fibroblasts," Lung Cell Mol Physiol 18:L119-L126 (1998).
Montesano et al., "Paracrine induction of angiogenesis in vitro by Swiss 3T3 fibroblasts," J Cell Science 105:1013-1024 (1993).
Chemical Engineering Technical Report 1992 vol. 24:86-91.
Clark and Greenberg, "Modulation of the effects of alveolar macrophages on lung fibroblast collagen production rate," Am Rev Respir Dis 134(1):52-56 (1987) Abstract.
Making Interferon, Chemtech Jul. 1989, pp. 428-430.
Thorpe, "Packed with Culture," Laboratory Practice 39(3):16-18(1989).
Utsumi, "Interferon Production with Multiray Culture System on a Large Scale," J. Interferon Research 4(1):9-16 (1984).
Villanueva et al., "Stimulation of fibroblast collagen and total protein format an andothelial cell-derived factor," Circ Res 69(1):134-141 (1991) Abstract.
Barka, T. et al., "Transduction of TAT-HA-β-galactosidase Fusion Protein into Salivary Gland-derived Cells and Organ Cultures of the Developing Gland, and into Rat Submandibular Gland in Vivo," J. Histochem. Cytochem. 48(11):1453-1460 (2000).
Barnes, D. and Sato, G., "Methods for Growth of Cultured Cells in Serum-Free Medium," Anal. Biochem. 102:255 (1980).
Barnes, D. "Serum-Free Animal Cell Culture," Biotechniques 5(6):534-542 (1987).

(56) References Cited

OTHER PUBLICATIONS

Bell, E. et al., "Living Tissue Formed in vitro and Accepted as Skin-Equivalent Tissue of Full Thickness," Science 211:1052-1054 (1981).
Bell, E. et al., "Production of a tissue-like structure by contraction of collagen lattices by human fibroblasts of different proliferative potential in vitro," PNAS USA 76(3):1274-1278 (1979).
Boudreau, N.J. and Jones, P.L., "Extracellular matrix and integrin signalling: the shape of things to come," Biochem. J. 339:481-488 (1999).
Cell and Tissue Culture: Laboratory Procedures, pp. 29D:0.1-29D:0.4 (1996).
Derossi, D. et al., "Cell Internalization of the Third Helix of the Antennapedia Homeodomain Is Receptor-independant," J. Biol. Chem. 271(30):18188-18193 (1996).
Deuel, T.F., "Growth Factors" in *Principles of Tissue Engineering*, Lanza et al. (eds.), Academic Press, pp. 133-142 (1995).
Doillon, C.J. et al., "Fibroblast-Collagen Sponge Interactions and the Spatial Deposition of Newly Synthesized Collagen Fibers in vitro and in vivo," Scanning Electron Microscopy 111:1313-1320 (1984).
Engels, J.W. and Uhlmann, E., "Gene Synthesis, "Angew. Chem. Intl. Ed. 28:716-734 (1989).
Fawell, S. et al., "Tat-mediated delivery of heterologous proteins into cells," PNAS 91:664-668 (1994).
Flax, J.D. et al., "Engraftable human neural stem cells respond to developmental cues, replace neurons, and express foreign genes," Nat. Biotechnol. 16(11):1033-139 (1998).
Folkman, J. and Haudenschild, "Angiogenesis in vitro," Nature 288(5791):551-556 (1980).
Fontaine, A.R. and Hall, B.D., "Biocompatibility of echinoderm skeleton with mammalian cells in vitro: Preliminary evidence," J. Biomed. Materials Res. 15:61-71 (1981).
Freshney, R.I., "Culture of specific cell types," in *Culture of Animal Cells. A Manual of Basic Techniques*, $2^{nd}$ Ed., A.R. Liss, Inc., New York, Ch. 20, pp. 257-288(1987).
Frisen, J. et al., "Central nervous system stem cells in the embryo and adult," Cell Mol. Life Sci. 54(9):935-945 (1998).
Futaki Shiroh et al, "Arginine-rich peptides: An abundant source of membrane-permeable peptides having potential as carriers for intracellular protein delivery", Journal of Biological Chemistry, American Society of Biological Chemists, Baltimore, MD, US, vol. 276, No. 8, Nov. 17, 2000, pp. 5836-5840.
Geiger, B. et al., "Transmembrane Extracellular Matrix-Cytoskeleton Crosstalk," Nature Reviews Molecular Cell Biol. 2:793-803 (2001).
GIBCO BRL Products and Reference Guide 1997-1998.
Gibson, G.J. et al., "Synthesis of a Low Molecular Weight Collagen by Chondrocytes from the Presumptive Calcification Region of the Embryonic Chick Sterna: The Influence of Culture with Collagen Cells," J. Cell Biology 99:208-216 (1984).
Goey, H. et al., "Inhibition of early murine hemopoietic progenitor cell proliferation after in vivo locoregional administration of transforming growth factor-beta 1," J. Immunol. 143(3):877-880 (1989).
Gonzalez-Rubio, M. et al., "Oxidative stress induces tyrosine phosphorylation of PDGF alpha-and-beta-receptors and pp60c-src in mesangial cells," Kidney Int. 50(1):164-173 (1996).
Green and Thomas, "Pattern formation by cultured human epidermal cells: development of curved ridges resembling dermatoglyphs," Science 200(4348):1385-1388 (1978).
Jiang, W.G. and Harding, K.G., "Enhancement of wound tissue expansion and angiogenesis by matrix-embedded fibroblast (Dermagraft), a role of hepatocyte growth factor/scatter factor," Int. J. Mol. Med. 2:203-210 (1998).
Keller and Snodgrass, "Human embronic stem cells: the future is now," Nat. Med. 5(2):151-152 (1999).
Kielty et al., Collagen: the collagen family: structure, assembly and organization in the extracellular matrix, in *Connective Tissue and its Heritable Disorders: Molecular, Genetic and Medical Aspects*, Rocye and Steinmann (eds.), Wiley-Liss, Inc., New York, 1993, pp. 103-147.
Kohen, R. and Gati, I., "Skin low molecular weight antioxidants and their role in aging and in oxidative stress," Toxicology 148:149-157 (2000).
Kohen, R., "Skin antioxidants: their role in aging and in oxidative stress—New approaches for their evaluation," Biomed. Pharmacother. 53:181-192 (1999).
Kohen, R.et al., "Overall Low Molecular Weight Antioxidant Activity of Biological Fluids and Tissues by Cyclic Voltammetry," Methods of Enymol. 300:285-290 (1999).
Kruse and Miedema, "Production and characterization of multiple-layered populations of animal cells," J. Cell Biol. 27(2):273-279 (1965).
Kwon et al., "Transduction of Cu,Zn-superoxide dismutase mediated by an HIV-1 Tat protein basic domain into mammalian cells," FEBS Ltrs. 485:163-167 (2000).
Mansbridge, J. et al., "Three-Dimensional Fibroblast Culture Implant for the Treatment of Diabetic Foot Ulcers: Metabolic Activity and Therapeutic Range," Tissue Eng. 4(4):403-414 (1998).
Matsuda, T. et al., "Photoinduced prevention of tissue adhesion," ASAIO J. 38(3):M154-M157 (1992).
Matsuzaki, T. "Role of hair papilla cells on induction and regeneration processes of hair follicles," Wound Repair Regen. 6(6):524-530 (1998).
Mikayama et al., "Molecular cloning and functional expression of a cDNA encoding glycosylation-inhibiting factor," PNAS USA 90:10056-10060 (1993).
Miyachi, Y., "Photoaging from an oxidative standpoint," Dermatol. Sci. 9:79-86 (1995).
Naughton, G. "Dermal Equivalents," pp. 891-902, in Principles of Tissue Engineering, $2^{nd}$ ed., Lanza et al., eds., Academic Press, 2000.
Neeman, M. et al., "Regulation of angiogenesis by hypoxic stress: from solid tumours to the ovarian follicle," Int. J. Exp. Pathol. 78(2):57-70 (1997).
Noda and Camilliere, "In vivo stimulation of bone formation by transforming growth factor-beta," Endocrinology 124(6):2991-2994 (1989).
Oberley, T.D. et al., "Immunohistochemical Localization of Glutathione-S-transferase and Glutathione Peroxidase in Adult Syrian Hamster Tissues and During Kidney Development," Am J Pathology139(2):355-369 (1991).
Pachence, J.M. and Kohn, J., "Biodegradable Polymers", pp. 263-277, in Principles of Tissue Engineering, $2^{nd}$ ed., Lanza et al. eds. Academic Press, 2000.
Parenteau, N. "The First tissue-Engineered Products," Scientific American 280:83-84 (1999).
Pierce, G.F. et al., "In vivo incisional wound healing augmented by platelet-derived growth factor and recombinant c-sis gene homodimeric proteins," J. exp. Med. 167(3):974-987 (1988).
Pietenpol, J.A. et al., "Transforming growth factor beta 1 suppression of c-myc gene transcription: role in inhibition of keratinocyte proliferation," PNAS USA 87(10):3758-3762 (1990).
Pinney et al., "Wound healing potential of Dermagraft (R) conditioned medium," J. Investig. Dermatol. 114(4):2000-2004 (2000).
Pinney et al., "Human three-dimensional fibroblast cultures expres agiogenic activity," J. Cell Physiol. 183(1):74-82(2000).
Pooga, M. et al., "Cell penetration by transportan," FASEB J. 12:67-77 (1998).
Ross, R. et al., "A platelet-dependent serum factor that stimulates the proliferation of arterial smooth muscle cells in vitro," PNAS USA 71(4):1207-1210 (1974).
Roy et al., "Simultaneous Detection of Tocopherols and Tocotrienols in Biological Samples Using HPLC-Coulometric Electrode Array," Meth. Enzymol.2002; 352: 326-32.
Royall, J.A. and Ischiropoulos, H., "Evaluation of 2",7"-Dichlorofluorescin and Dihydrorhodamine 123 as Fluorescent Probes for Intracellular $H_2O_2$ in Cultured Endothelial Cells," Arch. Biochem. Biophys. 302:348-355 (1993).
Schwarze, S. et al., "Protein transduction: unrestricted delivery into all cells?" Trends in Cell Biology 10:290-295 (2000).

(56) References Cited

OTHER PUBLICATIONS

Sen, C. et al., "Molecular basis of vitamin E action. Tocotrienol potently inhibits glutamate-induced pp60(c-Src) kinase activation and death of HT4 neuronal cells," J. Biol. Chem. 75(17):13049-13055 (2000).
Shamblott, M.J. et al., "Derivation of pluripotent stem cells from cultured human primordial germ cells," PNAS USA 95(23):13726-13731 (1998).
Smith, A., "Cell therapy: in search of pluripotency," Curr. Biol. 8(22):R802-804 (1998).
Sirica, A.E. et al., "Use of primary cultures of adult rat hepatocytes on collagen gel-nylon mesh to evaluate carcinogen-induced unscheduled DNA synthesis," Cancer Res. 40(9):3259-3265 (1980).
Sirica, A.E. et al., "Fetal phenotypic expression by adult rat hepatocytes on collagen gel/nylon meshes," PNAS USA 76(1):283-287 (1979).
Steffen, W., "Tat-mediated delivery of Antibodies into Cultured Cells," Methods in Mol. Biol. 161:141-148 (2001).
Stein, I. et al., "Stabilization of vascular endothelial growth factor mRNA by hypoxia and hypoglycemia and coregulation with other ischemia-induced genes," Mol. Cell Biol. 15(10):5363-5368 (1995).
Stephens, D.J. and Pepperkok, R., "The many ways to cross the plasma membrane," PNAS 98(8):4295-4298 (2001) www.pnas.org. cgi/doi/pnas.081065198.
Stohs, S.J., "The Role of Free Radicals in Toxicity and Disease," J. Basic Clin. Physio. Pharmacol. 6:206-228 (1995).
Thomas, J.A. et al., "Embryonic stem cell lines derived from human blastocysts," Science 282(5391):1145-1147 (1998).
Vives, E. et al., "A Truncated HIV-1 Tat Protein Basic Domain Rapidly Translocates through the Plasma Membrane and Accumulates in the Cell Nucleus," J. Biol. Chem. 272:16010-16017 (1997).
Voet, D. and Voet, J., Biochemistry, John Wiley & Sons, Inc. 1990, pp. 126-128 and 228-234.
Wells-Knecht, M.C. et al., "Age-dependent Increase in Ortho-Tyrosine and Methionine Sulfoxide in Human Skin Collagen Is Not Accelerated in Diabetes," J Clin Investig 100(4):839-846 (1997).
Williams, J.T. et al., "Cells isolated from adult human skeletal muscle capable of differentiating into multiple mesodermal phenotypes," Am. Surg. 65(1):22-26 (1999).
Yang and De Bono, "A new role for vascular endothelial growth factor and fibroblast growth factors: increasing endothelial resistance to oxidative stress," FEBS Lett. 403(2):139-442 (1997).
Yao, D.L. et al., "Cryogenic spinal cord injury induces astrocytic gene expression of insulin-like growth factor 1 and insulin-like growth factor binding protein 2 during myelin regeneration," J. Neurosci. Res. 40(5):647-659 (1995).
PCT/US02/18057 WO Search Report dated Oct. 7, 2002.
WO00/069449 Search Report dated Nov. 29, 2000.
WO02/098365 Search Report dated Jan. 15, 2003.
EP02744248.2 Search Report dated Feb. 3, 2005.
United States Court of Appeals for the Federal Circuit, Decision No. 2012-1560, dated Aug. 23, 2013, Appeal from the United States District Court for the Southern District of California, Case No. 09-CV-0122, 51 pages.

* cited by examiner

CONDITIONED CELL CULTURE MEDIUM COMPOSITIONS AND METHODS OF USE

CROSS-REFERENCE

This application is a continuation of U.S. patent application Ser. No. 13/417,017, filed Mar. 9, 2012, which is a continuation of U.S. patent application Ser. No. 12/349,451, filed Jan. 6, 2009, now U.S. Pat. No. 8,138,147; which is a divisional of U.S. patent application Ser. No. 11/538,380 filed Oct. 3, 2006, now U.S. Pat. No. 8,361,485; which is a divisional of Ser. No. 09/979,813 filed on Jul. 19, 2002, now U.S. Pat. No. 7,118,746; which is a 371 U.S. National Phase Application of PCT/US00/13016 filed May 12, 2000; which is a continuation-in-part of U.S. patent application Ser. No. 09/313,538 filed May 14, 1999, now U.S. Pat. No. 6,372,494. The disclosures of each of the above-referenced applications are hereby incorporated by reference in their entirety.

INTRODUCTION

The invention relates to compositions comprising cell culture medium conditioned by cells grown in two-dimensional culture (i.e., a monolayer), or in three-dimensional culture. The cells used to condition the medium may be genetically modified to alter the concentration of proteins found in the medium. The conditioned cell medium is processed for uses which include wound applications, cosmetic additives, food supplements, animal feed supplements, culturing cells, pharmaceutical applications, as well as compositions and methods for stimulating hair growth. The invention also relates to compositions containing extracellular matrix proteins and/or other purified protein(s) derived from the conditioned medium.

BACKGROUND OF THE INVENTION

Conditioned Cell Media

Culture medium compositions typically include essential amino acids, salts, vitamins, minerals, trace metals, sugars, lipids and nucleosides. Cell culture medium attempts to supply the components necessary to meet the nutritional needs required to grow cells in a controlled, artificial and in vitro environment. Nutrient formulations, pH, and osmolarity vary in accordance with parameters such as cell type, cell density, and the culture system employed. Many cell culture medium formulations are documented in the literature and a number of media are commercially available. Once the culture medium is incubated with cells, it is known to those skilled in the art as "spent" or "conditioned medium". Conditioned medium contains many of the original components of the medium, as well as a variety of cellular metabolites and secreted proteins, including, for example, biologically active growth factors, inflammatory mediators and other extracellular proteins. Cell lines grown as a monolayer or on beads, as opposed to cells grown in three-dimensions, lack the cell-cell and cell-matrix interactions characteristic of whole tissue in vivo. Consequently, such cells secrete a variety of cellular metabolites although they do not necessarily secrete these metabolites and secreted proteins at levels that approach physiological levels. Conventional conditioned cell culture medium, medium cultured by cell-lines grown as a monolayer or on beads, is usually discarded or occasionally used in culture manipulations such as reducing cell densities.

Tissue Culture Systems

The majority of vertebrate cell cultures in vitro are grown as monolayers on an artificial substrate bathed in culture medium. The nature of the substrate on which the monolayers grow may be solid, such as plastic, or semisolid gels, such as collagen or agar. Disposable plastics have become the preferred substrate used in modern-day tissue or cell culture.

A few researchers have explored the use of natural substrates related to basement membrane components. Basement membranes comprise a mixture of glycoproteins and proteoglycans that surround most cells in vivo. For example, Reid and Rojkund, 1979, In, *Methods in Enzymology*, Vol. 57, *Cell Culture*, Jakoby & Pasten, eds., New York, Acad. Press, pp. 263-278; Vlodaysky et al., 1980, Cell 19:607-617; Yang et al., 1979, *Proc. Natl. Acad. Sci. USA* 76:3401 have used collagen for culturing hepatocytes, epithelial cells and endothelial tissue. Growth of cells on floating collagen (Michalopoulos and Pitot, 1975, Fed. Proc. 34:826) and cellulose nitrate membranes (Savage and Bonney, 1978, *Exp. Cell Res.* 114:307-315) have been used in attempts to promote terminal differentiation. However, prolonged cellular regeneration and the culture of such tissues in such systems have not heretofore been achieved.

Cultures of mouse embryo fibroblasts have been used to enhance growth of cells, particularly at low densities. This effect is thought to be due partly to supplementation of the medium but may also be due to conditioning of the substrate by cell products. In these systems, feeder layers of fibroblasts are grown as confluent monolayers which make the surface suitable for attachment of other cells. For example, the growth of glioma on confluent feeder layers of normal fetal intestine has been reported (Lindsay, 1979, *Nature* 228:80).

While the growth of cells in two dimensions is a convenient method for preparing, observing and studying cells in culture, allowing a high rate of cell proliferation, it lacks characteristic of whole tissue in vivo. In order to study such functional and morphological interactions, a few investigators have explored the use of three-dimensional substrates such as collagen gel (Douglas et al., 1980, *In Vitro* 16:306-312; Yang et al., 1979, *Proc. Natl. Acad. Sci.* 76:3401; Yang et al., 1980, *Proc. Natl. Acad. Sci.* 77:2088-2092; Yang et al., 1981, *Cancer Res.* 41:1021-1027); cellulose sponge, alone (Leighton et al., 1951, *J. Natl. Cancer Inst.* 12:545-561) or collagen coated (Leighton et al., 1968, *Cancer Res.* 28:286-296); a gelatin sponge, Gelfoam (Sorour et al., 1975, *J. Neurosurg.* 43:742-749).

In general, these three-dimensional substrates are inoculated with the cells to be cultured. Many of the cell types have been reported to penetrate the matrix and establish a "tissue-like" histology. For example, three-dimensional collagen gels have been utilized to culture breast epithelium (Yang et al., 1981, *Cancer Res.* 41:1021-1027) and sympathetic neurons (Ebendal, 1976, *Exp. Cell Res.* 98:159-169). Additionally, various attempts have been made to regenerate tissue-like architecture from dispersed monolayer cultures. (Kruse and Miedema, 1965, *J. Cell Biol.* 27:273) reported that perfused monolayers could grow to more than ten cells deep and organoid structures can develop in multilayered cultures if kept supplied with appropriate medium (see also Schneider et al., 1963, *Exp. Cell. Res.* 30:449-459; Bell et al., 1979, *Proc. Natl. Acad. Sci. USA* 76:1274-1279; Green, 1978, *Science* 200:1385-1388). It has been reported that human epidermal keratinocytes may form dematoglyphs (friction ridges if kept for several weeks without transfer;

Folkman and Haudenschild (1980, *Nature* 288:551-556) reported the formation of capillary tubules in cultures of vascular endothelial cells cultured in the presence of endothelial growth factor and medium conditioned by tumor cells; and Sirica et al. (1979, *Proc. Natl. Acad. Sci. USA* 76:283-287; 1980, *Cancer Res.* 40:3259-3267) maintained hepatocytes in primary culture for about 10-13 days on nylon meshes coated with a thin layer of collagen. However, the long term culture and proliferation of cells in such systems has not been achieved.

The establishment of long term culture of tissues such as bone marrow has been attempted. Overall the results were disappointing, in that although a stromal cell layer containing different cell types is rapidly formed, significant hematopoiesis could not be maintained for any real time. (For review see Dexter et al., In *Long Term Bone Marrow Culture*, 1984, Alan R. Liss, Inc., pp. 57-96).

A number of groups have attempted to grow skin and connective tissue in vitro for transplantation in vivo. In one such system, a hydrated bovine collagen lattice forms the substrate to which cells, such as fibroblasts are incorporated which results in the contraction of the lattice into tissue (Bell et al., U.S. Pat. No. 4,485,096). In another system, a porous cross-linked collagen sponge is used to culture fibroblast cells (Eisenberg, WO 91/16010). A scaffold composed of synthetic polymers has also been described to control cell growth and proliferation in vitro so that once the fibroblasts begin to grow and attach to the matrix it is transplanted into the patient (Vacanti et al., U.S. Pat. Nos. 5,759,830; 5,770,193; 5,736,372).

Synthetic matrices composed of biodegradable, biocompatible copolymers of polyesters and amino acids have also been designed as scaffolding for cell growth (U.S. Pat. Nos. 5,654,381; 5,709,854). Non-biodegradable scaffolds are likewise capable of supporting cell growth. Three-dimensional cell culture systems have also been designed which are composed of a stromal matrix which supports the growth of cells from any desired tissue into an adult tissue (Naughton et al., U.S. Pat. Nos. 4,721,096 and 5,032,508). Another approach involves slowly polymerizing hydrogels containing large numbers of the desired cell type which harden into a matrix once administered to a patient (U.S. Pat. No. 5,709,854). Extracellular matrix preparations have been designed which are composed of stromal cells which provide a three dimensional cell culture system for a desired cell type which may be injected into the patient for precise placement of the biomaterial (Naughton et al., WO 96/39101).

Cellular Cytokines and Growth Factors

The secretion of extracellular proteins into conditioned cell media such as growth factors, cytokines, and stress proteins opens new possibilities in the preparation of products for use in a large variety of areas including tissue repair, e.g., in the treatment of wounds and other tissue defects such as cosmetic defects as well as human and animal feed supplements. For example, growth factors are known to play an important role in the wound healing process. In general, it is thought desirable in the treatment of wounds to enhance the supply of growth factors by direct addition of these factors.

Cellular cytokines and growth factors are involved in a number of critical cellular processes including cell proliferation, adhesion, morphologic appearance, differentiation, migration, inflammatory responses, angiogenesis, and cell death. Studies have demonstrated that hypoxic stress and injury to cells induce responses including increased levels of mRNA and proteins corresponding to growth factors such as PDGF (platelet-derived growth factor), VEGF (vascular endothelial growth factor), FGF (fibroblast growth factor), and IGF (insulin-like growth factor) (Gonzalez-Rubio, M. et al., 1996, *Kidney Int.* 50(1):164-73; Abramovitch, R. et al., 1997, *Int J Exp. Pathol.* 78(2):57-70; Stein, I. et al., 1995, *Mol Cell Biol.* 15(10):5363-8; Yang, W. et al., 1997, FEBS Lett. 403(2):139-42; West, N. R. et al., 1995, *J. Neurosci. Res.* 40(5):647-59).

Growth factors, such as transforming growth factor-β, also known in the art as TGF-β, are induced by certain stress proteins during wound healing. Two known stress proteins are GRP78 and HSP90. These proteins stabilize cellular structures and render the cells resistant to adverse conditions. The TGF-β family of dimeric proteins includes TGF-β1, TGF-β2, and TGF-β3 and regulates the growth and differentiation of many cell types. Furthermore, this family of proteins exhibits a range of biological effects, stimulating the growth of some cell types (Noda et al., 1989, *Endocrinology* 124:2991-2995) and inhibiting the growth of other cell types (Goey et al., 1989, *J. Immunol.* 143:877-880; Pietenpol et al., 1990, *Proc. Natl. Acad. Sci. USA* 87:3758-3762). TGF-β has also been shown to increase the expression of extracellular matrix proteins including collagen and fibronectin (Ignotz et al., 1986, *J. Biol. Chem.* 261:4337-4345) and to accelerate the healing of wounds (Mustoe et al., 1987, *Science* 237:1333-1335).

Another such growth factor is PDGF. PDGF was originally found to be a potent mitogen for mesenchymal-derived cells (Ross R. et al., 1974, *Proc. Natl. Acad. Sci. USA* 71(4):1207-1210; Kohler N. et al., 1974, *Exp. Cell Res.* 87:297-301). Further studies have shown that PDGF increases the rate of cellularity and granulation in tissue formation. Wounds treated with PDGF have the appearance of an early stage inflammatory response including an increase in neutrophils and macrophage cell types at the wound site. These wounds also show enhanced fibroblast function (Pierce, G. F. et al., 1988, *J. Exp. Med.* 167:974-987). Both PDGF and TGF-β have been shown to increase collagen formation, DNA content, and protein levels in animal studies (Grotendorst, G. R. et al., 1985, *J. Clin. Invest.* 76:2323-2329; Sporn, M. B. et al., 1983, *Science* (Wash D.C.) 219:1329). PDGF has been shown to be effective in the treatment of human wounds. In human wounds, PDGF-AA expression is increased within pressure ulcers undergoing healing. The increase of PDGF-AA corresponds to an increase in activated fibroblasts, extracellular matrix deposition, and active vascularization of the wound. Furthermore, such an increase in PDGF-AA is not seen in chronic non-healing wounds (Principles of Tissue Engineering, R. Lanza et al. (eds.), pp. 133-141 (R.G. Landes Co. TX 1997). A number of other growth factors having the ability to induce angiogenesis and wound healing include VEGF, KGF and basic FGF.

There are currently no simple effective methods or compositions for application containing the variety of cytokines, growth factors or other regulatory proteins found in Applicants' conditioned media.

SUMMARY OF THE INVENTION

The Applicants of the present invention have discovered novel conditioned cell culture medium compositions. Additionally, the invention comprises uses for these novel compositions. The invention further comprises compositions containing particular protein products derived from the conditioned cell media of the invention.

The conditioned cell medium compositions of the invention may be comprised of any known defined or undefined medium and may be conditioned using any eukaryotic cell type. The medium may be conditioned by stromal cells, parenchymal cells, mesenchymal stem cells, liver reserve cells, neural stem cells, pancreatic stem cells, and/or embryonic stem cells. A three-dimensional tissue construct is preferred. The cell type, whether in monolayer or in three-dimensions, will affect the properties of the conditioned medium. For example, a medium conditioned with astrocytes and neuronal cells will elaborate certain characteristic metabolites and proteins so that such a conditioned medium is preferred for certain nerve repair applications. In a preferred embodiment, Applicants' medium is conditioned with a three-dimensional cell and tissue culture. In another preferred embodiment, the medium is conditioned with the stromal cells used in the production of TransCyte™ (Smith & Nephew PLC., United Kingdom). In a highly preferred embodiment, cells of the three-dimensional tissue culture are stromal cells and the tissue culture construct is Dermagraft® (Advanced Tissue Sciences, Inc., La Jolla Calif.) with or without the addition of specific parenchymal cells. Such conditioned cell medium provides a unique combination of factors and specified ratios that are different than monolayer cultures and more closely represent those found in vivo. The three-dimensional stromal culture may further be cultured with parenchymal cells such as the cells of the skin, bone, liver, nerve, pancreas, etc., resulting in a conditioned medium containing characteristic extracellular proteins and other metabolites of that tissue type. Additionally, each cell type may also be genetically modified. The genetic modification may be used to alter the concentration of one or more component in the medium such as, for example, to upregulate a protein, to introduce a new protein, or to regulate ion concentration.

Once the cell medium of the invention is conditioned, it may be used in any state. Physical embodiments of the conditioned medium include, but are not limited to, liquid or solid, frozen, lyophilized or dried into a powder. Additionally, the medium may be formulated with a pharmaceutically acceptable carrier as a vehicle for internal administration, applied directly to a food item or product, formulated with a salve or ointment for topical applications, or, for example, made into or added to surgical glue to accelerate healing of sutures following invasive procedures. Also, the medium may be further processed to concentrate or reduce one or more factors or components contained within the medium. For example, the conditioned medium may be enriched with a growth factor by using immunoaffinity chromatography.

In one embodiment, the conditioned medium of the invention is used in wound healing. Examples include, but are not limited to, applying the conditioned cell medium to the gauze of a bandage (adhesive or non-adhesive) and used in topical applications to promote and/or accelerate wound healing. Again, the conditioned medium may be processed to concentrate or reduce one or more components to enhance wound healing. The compositions may be lyophilized/freeze-dried and added as a wound filler or added to existing wound filling compositions to accelerate wound healing. Alternatively, the medium may be added to a hydrogel composition and used as a film for topical wound treatments and anti-adhesion applications. The medium compositions of the invention may be conditioned with cells which express gene products with improved wound-healing properties; i.e., engineered cells which express gene products that have anti-scarring properties.

In another embodiment, the conditioned cell medium formulations of the invention are used to correct congenital anomalies and acquired physical defects. Further, formulations in the form of injectables or hydrogels may be used to eliminate wrinkles, frown lines, scarring and to repair other skin conditions. In another embodiment, the conditioned cell medium may also be added to eye shadow, pancake makeup, compacts or other cosmetics.

In yet another embodiment, the conditioned cell media formulations of the invention are used as food additives and dietary supplements. The conditioned medium contains a multitude of nutrients including essential amino acids, vitamins, and minerals. The conditioned cell media of the invention may be concentrated and/or lyophilized, for example, and are preferably administered in capsules or tablets for ingestion. Additionally, the compositions can also be added directly to food to enhance its nutritional content.

In a further embodiment, the compositions may be used as a supplement to animal feed as it contains a variety of proteins vitamins, antibiotics, polysaccharides and other factors beneficial for raising cattle and other ruminant animals.

In yet another embodiment of the invention, the compositions of the invention may be used to culture cells. The conditioned cell media of the invention contains factors useful in promoting cell attachment and growth. Further, the cell medium may be conditioned by cells which are genetically engineered and which may, for example, contain increased fibronective or collagen concentrations beneficial in promoting cell attachment to a scaffold or culture surface.

In an additional embodiment of the invention, the conditioned cell medium compositions of the invention are used for pharmaceutical applications. The invention comprises cell media cultured with three-dimensional tissue constructs, such that, growth factors and other proteins are secreted into the medium at ratios closely resembling those found in vivo. As such, the conditioned media of the invention is beneficial for a variety of pharmaceutical applications.

Lastly, the compositions of the invention may be formulated for topical applications for stimulating hair growth.

DEFINITIONS

The following terms used herein shall have the meanings indicated:

Adherent Layer: cells attached directly to the three-dimensional support or connected indirectly by attachment to cells that are themselves attached directly to the support.

Conditioned Medium: a formulation containing extracellular protein(s) and cellular metabolites, which has previously supported the growth of any desired eukaryotic cell type, said cells having been cultured in either two or three dimensions. Also called "Conditioned Cell Medium" or "Conditioned Cell and Tissue Culture Medium".

Stromal Cells: fibroblasts with or without other cells and/or elements found in loose connective tissue, including but not limited to, endothelial cells, pericytes, macrophages, monocytes, plasma cells, mast cells, adipocytes, mesenchymal stem cells, liver reserve cells, neural stem cells, pancreatic stem cells, chondrocytes, prechondrocytes, etc.

Tissue-Specific or Parenchymal Cells: the cells which form the essential and distinctive tissue of an organ as distinguished from its supportive framework.

Three-Dimensional Framework: a three-dimensional scaffold composed of any material and/or shape that (a) allows cells to attach to it (or can be modified to allow cells to attach to it); and (b) allows cells to grow in more than one layer. This support is inoculated with stromal cells to form the living three-dimensional stromal tissue. The structure of the framework can include a mesh, a sponge or can be formed from a hydrogel.

Three-Dimensional Stromal Tissue or Living Stromal Matrix: a three-dimensional framework which has been inoculated with stromal cells that are grown on the support. The extracellular matrix proteins elaborated by the stromal cells are deposited onto the framework, thus forming a living stromal tissue. The living stromal tissue can support the growth of tissue-specific cells later inoculated to form the three-dimensional cell culture.

Tissue-Specific Three-Dimensional Cell Culture or Tissue-Specific Three-Dimensional Construct: a three-dimensional living stromal tissue which has been inoculated with tissue-specific cells and cultured. In general, the tissue specific cells used to inoculate the three-dimensional stromal matrix should include the "stem" cells (or "reserve" cells) for that tissue; i.e., those cells which generate new cells that will mature into the specialized cells that form the parenchyma of the tissue.

The following abbreviations shall have the meanings indicated:

BCS=bovine calf serum
BFU-E=burst-forming unit-erythroid
TGF-β=transforming growth factor-β
CFU-C=colony forming unit-culture
CFU-GEMM=colony forming unit-granuloid, erythroid, monocyte, megakaryocyte
CSF=colony-stimulating factor
DMEM=Dulbecco's Modified Eagle's Medium
EDTA=ethylenediamine tetraacetic acid
FBS=fetal bovine serum
FGF=fibroblast growth factor
GAG=glycosaminoglycan
GM-CSF=granulocyte/macrophage colony-stimulating factor
HBSS=Hank's balanced salt solution
HS=horse serum
IGF=insulin-like growth factor
LTBMC=long term bone marrow culture
MEM=minimal essential medium
PBL=peripheral blood leukocytes
PBS=phosphate buffered saline
PDGF=platelet-derived growth factor
RPMI 1640=Roswell Park Memorial Institute medium number 1640 (GIBCO, Inc., Grand Island, N.Y.)
SEM=scanning electron microscopy
VEGF=vascular endothelial growth factor

DETAILED DESCRIPTION OF THE INVENTION

Figure 1:
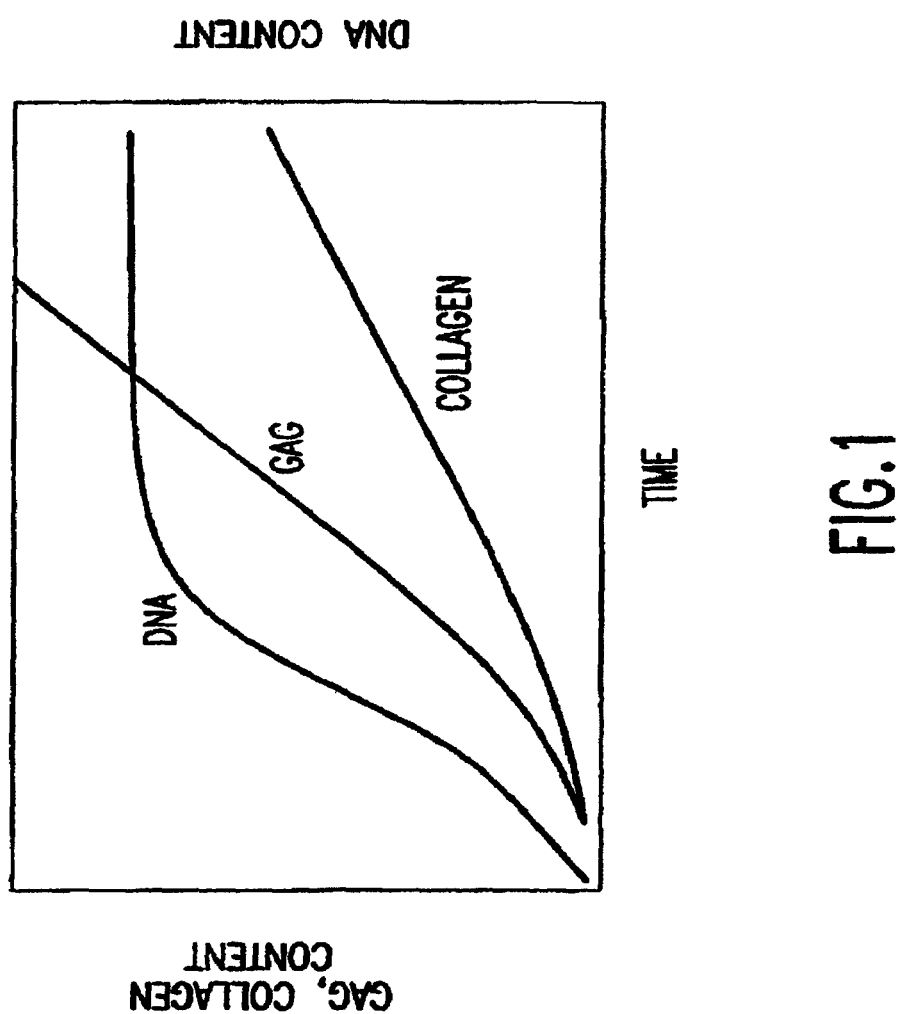
FIG. 1 is a graph representing the kinetics of the deposition of glycosaminoglycans and collagen laid down over time by the three-dimensional tissue products Transcyte™ and Dermagraft®. The deposition volumes of the glycosaminoglycans are dependent on the period of growth while the deposition of collagen is not dependent on the period of growth.

The present invention relates to novel compositions comprising any conditioned defined or undefined medium, cultured using any eukaryotic cell type or three-dimensional tissue construct and methods for using the compositions. The cells are cultured in monolayer, beads (i.e., two-dimensions) or, preferably, in three-dimensions. The cells are preferably human to reduce the risk of an immune response and include stromal cells, parenchymal cells, mesenchymal stem cells, liver reserve cells, neural stem cells, pancreatic stem cells and/or embryonic stem cells. Medium conditioned by cell and tissue cultures will contain a variety of naturally secreted proteins, such as biologically active growth factors and those cultured in three-dimensions will have these proteins in ratios approaching physiological levels. The invention also relates to novel compositions comprising products derived from the conditioned cell media and uses for these compositions.

The "pre-conditioned" cell culture medium may be any cell culture medium which adequately addresses the nutritional needs of the cells being cultured. Examples of cell media include, but are not limited to Dulbecco's Modified Eagle's Medium (DMEM), Ham's F12, RPMI 1640, Iscove's, McCoy's and other media formulations readily apparent to those skilled in the art, including those found in *Methods For Preparation of Media, Supplements and Substrate For Serum-Free Animal Cell Culture* Alan R. Liss, New York (1984) and *Cell & Tissue Culture: Laboratory Procedures*, John Wiley & Sons Ltd., Chichester, England 1996, both of which are incorporated by reference herein in their entirety. The medium may be supplemented, with any components necessary to support the desired cell or tissue culture. Additionally serum, such as bovine serum, which is a complex solution of albumins, globulins, growth promoters and growth inhibitors may be added if desired. The serum should be pathogen free and carefully screened for mycoplasma bacterial, fungal, and viral contamination. Also, the serum should generally be obtained from the United States and not obtained from countries where indigenous livestock carry transmittable agents. Hormone addition into the medium may or may not be desired.

Other ingredients, such as vitamins, growth and attachment factors, proteins etc., can be selected by those of skill in the art in accordance with his or her particular need. The present invention may use any cell type appropriate to achieve the desired conditioned medium. Genetically engineered cells may be used to culture the media. Such cells can be modified, for example, to express a desired protein or proteins so that the concentration of the expressed protein or proteins in the medium is optimized for the particular desired application. In accordance with the present invention, the cells and tissue cultures used to condition the medium may be engineered to express a target gene product which may impart a wide variety of functions, including but not limited to, improved properties in expressing proteins resembling physiological reactions, increased expression of a particular protein useful for a specific application, such as wound healing or inhibiting certain proteins such as proteases, lactic acid, etc.

The cells may be engineered to express a target gene product which is biologically active which provides a chosen biological function, which acts as a reporter of a chosen physiological condition, which augments deficient or defective expression of a gene product, or which provides an anti-viral, anti-bacterial, anti-microbial, or anti-cancer activity. In accordance with the present invention, the target gene product may be a peptide or protein, such as an enzyme, hormone, cytokine, antigen, or antibody, a regulatory protein, such as a transcription factor or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may upregulate an endogenous protein, introduce a new protein or regulate ion concentration by expressing a heterologous ion channel or altering endogenous ion channel function. Examples include, but are not limited to engineered tissues that express gene products which are delivered systemically (e.g., secreted gene products such as proteins including growth factors, hormones, Factor VIII, Factor IX, neurotransmitters, and enkaphalins).

In the present invention, it is preferred that the cells are grown on a three-dimensional stromal support and grow in multiple layers, forming a cellular matrix. This matrix system approaches physiologic conditions found in vivo to a greater degree than previously described monolayer tissue culture systems. Three-dimensional cultures, such as Dermagraft® (Advanced Tissue Sciences, Inc., La Jolla, Calif.) "Dermagraft®", and TransCyte™ (Smith & Nephew, PLC, United Kingdom) "Transcyte™", produce numerous growth factors and other proteins that are secreted into the medium at physiological ratios and concentrations. Dermagraft® is composed of allogeneic neonatal fibroblasts cultured on biodegradable polyglactin. TransCyte™ is a temporary living skin replacement comprising a three-dimensional stromal tissue bonded to a transitional covering as described in U.S. Pat. No. 5,460,939. Additionally, the three-dimensional tissue cultures which condition the cell media may contain mesenchymal stem cells, liver reserve cells, neural stem cells, pancreatic stem cells, and/or embryonic stem cells and/or parenchymal cells and/or parenchymal stem cells found in many tissue types, including but not limited to bone marrow, skin, liver, pancreas, kidney, adrenal and neurologic tissue, as well as tissues of the gastrointestinal and genitourinary tracts, and the circulatory system. See U.S. Pat. Nos. 4,721,096; 4,963,489; 5,032,508; 5,266,480; 5,160,490; and 5,559,022, each of which is incorporated by reference herein in their entirety.

Cell Media

Cell culture media formulations are well known in the literature and many are commercially available.

Preconditioned media ingredients include, but are not limited to those described below. Additionally, the concentration of the ingredients is well known to one of ordinary skill in the art. See, for example, *Methods For Preparation Of Media, Supplements and Substrate for Serum-free Animal Cell Cultures*, supra. The ingredients include amino-acids (both D and/or L-amino acids) such as glutamine, alanine, arginine, asparagine, cysteine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates.

Additional ingredients include sugars, deoxyribose, ribose, nucleosides, water soluble vitamins, riboflavin, salts, trace metals, lipids, acetate salts, phosphate salts, HEPES, phenol red, pyruvate salts and buffers.

Other ingredients often used in media formulations include fat soluble vitamins (including A, D, E and K) steroids and their derivatives, cholesterol, fatty acids and lipids Tween 80, 2-mercaptoethanol pyramidines as well as a variety of supplements including serum (fetal, horse, calf, etc.), proteins (insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.).

Of course, the media may or may not need to be supplemented with growth factors and other proteins such as attachment factors since many of the cell constructs, particularly the three-dimensional cell and tissue culture constructs described in this application themselves elaborate such growth and attachment factors and other products into the media as discussed in greater detail infra, Section 5.8.

The Cell Cultures

The Cells

The medium may be conditioned by stromal cells, parenchymal cells, mesenchymal stem cells (lineage committed or uncommitted progenitor cells), liver reserve cells, neural stem cells, pancreatic stem cells, and/or embryonic stem cells. The cells may include, but are not limited to, bone marrow, skin, liver, pancreas, kidney, neurological tissue, adrenal gland, mucosal epithelium, and smooth muscle, to name but a few. The fibroblasts and fibroblast-like cells and other cells and/or elements that comprise the stroma may be fetal or adult in origin, and may be derived from convenient sources such as skin, liver, pancreas, mucosa, arteries, veins, umbilical cord, and placental tissues, etc. Such tissues and/or organs can be obtained by appropriate biopsy or upon autopsy. In fact, cadaver organs may be used to provide a generous supply of stromal cells and elements.

Embryonic stem cells and/or other elements that comprise the stroma may be isolated using methods known in the art. For instance, recently human embryonic stem cell populations and methods for isolating and using these cells have been reported in Keller et al., *Nature Med.*, 5:151-152 (1999), Smith *Curr. Biol.* 8:R802-804 (1998); isolated from primordial germ cells, Shamblatt et al., *PNAS* 95:13726-1373 (1998), isolated from blastocytes Thomason et al., *Science* 282:1145-1147 (1988). The isolation and culture of mesenchymal stem cells are known in the art. See Mackay et al., *Tissue Eng.* 4:415-428 (1988); William et al., *Am Surg.* 65:22-26 (1999). Inoculation of these cells is described infra, in Section 5.3. Likewise, neural stem cells may be isolated in the manner described in Flax et al., *Nature Biotechnol.*, 16:1033-1039 (1998); and Frisen et al., *Cell. Mol. Life Sci.*, 54:935-945 (1998).

The cells may be cultured in any manner known in the art including in monolayer, beads or in three-dimensions and by any means (i.e., culture dish, roller bottle, a continuous flow system, etc.). Methods of cell and tissue culturing are well known in the art, and are described, for example, in *Cell & Tissue Culture: Laboratory Procedures*, supra, Freshney (1987), *Culture of Animal Cells: A Manual of Basic Techniques*, infra.

In general, the cell lines utilized are carefully screened for human and animal pathogens. Depending upon the application, such screening may be of critical importance where only pathogen free cells are acceptable (e.g., for wound healing, food additives, etc.) Methods of screening for pathogens are well known in the art. The cell type, whether cultured in two-dimensions or three-dimensions, will affect the properties of the conditioned medium. A three-dimensional construct is preferred.

Three-Dimensional Cell Cultures

The stromal cells used in the three-dimensional cultures comprise fibroblasts, mesenchymal stem cells, liver reserve cells, neural stem cells, pancreatic stem cells, and/or embryonic stem cells with or without additional cells and/or elements described more fully herein.

Fibroblasts will support the growth of many different cells and tissues in the three-dimensional culture system, and, therefore, can be inoculated onto the matrix to form a "generic" stromal support matrix for culturing any of a variety of cells and tissues. However, in certain instances, it may be preferable to use a "specific" rather than "generic" stromal support matrix, in which case stromal cells and elements can be obtained from a particular tissue, organ, or individual. Moreover, fibroblasts and other stromal cells and/or elements may be derived from the same type of tissue to be cultured in the three-dimensional system. This might be advantageous when culturing tissues in which specialized stromal cells may play particular structural/functional roles; e.g., smooth muscle cells of arteries, glial cells of neurological tissue, Kupffer cells of liver, etc.

Once inoculated onto the three-dimensional support, the stromal cells will proliferate on the framework and deposit the connective tissue proteins naturally secreted by the stromal cells such as growth factors, regulatory factors and extracellular matrix proteins. The stromal cells and their naturally secreted connective tissue proteins substantially envelop the framework thus forming the living stromal tissue which will support the growth of tissue-specific cells inoculated into the three-dimensional culture system of the invention. In fact, when inoculated with the tissue-specific cells, the three-dimensional stromal tissue will sustain active proliferation of the culture for long periods of time. Importantly, because openings in the mesh permit the exit of stromal cells in culture, confluent stromal cultures do not exhibit contact inhibition, and the stromal cells continue to grow, divide, and remain functionally active.

Growth and regulatory factors are elaborated by the stromal tissue into the media. Growth factors (for example, but not limited to, αFGF, βFGF, insulin growth factor or TGF-betas), or natural or modified blood products or other bioactive biological molecules (for example, but not limited to, hyaluronic acid or hormones), enhance the colonization of the three-dimensional framework or scaffolding and condition the culture media.

The extent to which the stromal cells are grown prior to use of the cultures in vivo may vary depending on the type of tissue to be grown in three-dimensional tissue culture. The living stromal tissues which condition the medium may be used as corrective structures by implanting them in vivo. Alternatively, the living stromal tissues may be inoculated with another cell type and implanted in vivo. The stromal cells may be genetically engineered to adjust the level of protein products secreted into the culture medium to improve the concentration of recovered product obtained from the conditioned medium. For example, anti-inflammatory factors, e.g., anti-GM-CSF, anti-TNF, anti-IL-1, anti-IL-2, etc. Alternatively, the stromal cells may be genetically engineered to "knock out" expression of native gene products that promote inflammation, e.g., GM-CSF, TNF, IL-1, IL-2, or "knock out" expression of MHC in order to lower the risk of rejection.

Growth of the stromal cells in three-dimensions will sustain active proliferation of both the stromal and tissue-specific cells in culture for much longer time periods than will monolayer systems. Moreover, the three-dimensional system supports the maturation, differentiation, and segregation of cells in culture in vitro to form components of adult tissues analogous to counterparts found in vivo and secure proteins into the conditional medium more closely resembling physiological ratios.

Although the Applicants are under no duty or obligation to explain the mechanism by which the three-dimensional cell and tissue and the works, a number of factors inherent in the three-dimensional culture system may contribute to its success:

(a) The three-dimensional framework provides a greater surface area for protein attachment, and consequently, for the adherence of stromal cells; and (b) Because of the three-dimensionality of the framework, stromal cells continue to grow actively, in contrast to cells in monolayer cultures, which grow to confluence, exhibit contact inhibition, and cease to grow and divide. The elaboration of growth and regulatory factors by replicating stromal cells may be partially responsible for stimulating proliferation and regulating differentiation of cells in culture;

(c) The three-dimensional framework allows for a spatial distribution of cellular elements which is more analogous to that found in the counterpart tissue in vivo;

(d) The increase in potential volume for cell growth in the three-dimensional system may allow the establishment of localized microenvironments conducive to cellular maturation;

(e) The three-dimensional framework maximizes cell-cell interactions by allowing greater potential for movement of migratory cells, such as macrophages, monocytes and possibly lymphocytes in the adherent layer;

(f) It has been recognized that maintenance of a differentiated cellular phenotype requires not only growth/differentiation factors but also the appropriate cellular interactions. The present invention effectively recreates the tissue microenvironment resulting in a superior conditioned medium.

Establishment of Three-Dimensional Stromal Tissue

The three-dimensional support or framework may be of any material and/or shape that: (a) allows cells to attach to it (or can be modified to allow cells to attach to it); and (b) allows cells to grow in more than one layer. A number of different materials may be used to form the framework, including but not limited to: non-biodegradable materials, e.g., nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton; and biodegradable materials, e.g., polyglycolic acid (PGA), collagen, collagen sponges, cat gut sutures, cellulose, gelatin, dextran, polyalkanoates, etc. Any of these materials may be woven braided, knitted, etc., into a mesh, for example, to form the three-dimensional framework. The framework, in turn can be fashioned into any shape desired as the corrective structure, e.g., tubes, ropes, filaments, etc. Certain materials, such as nylon, polystyrene, etc., are poor substrates for cellular attachment. When these materials are used as the three-dimensional framework, it is advisable to pre-treat the framework prior to inoculation of stromal cells in order to enhance the attachment of stromal cells to the support. For example, prior to inoculation with stromal cells, nylon frameworks could be treated with 0.1M acetic acid, and incubated in polylysine, FBS, and/or collagen to coat the nylon. Polystyrene could be similarly treated using sulfuric acid.

When the cultures conditioning the medium are to be implanted in vivo, it may be preferable to use biodegradable matrices such as polyglycolic acid, collagen, collagen sponges, woven collagen, catgut suture material, gelatin, polylactic acid, or polyglycolic acid and copolymers thereof, for example. Where the cultures are to be maintained for long periods of time or cryopreserved, non-degradable materials such as nylon, dacron, polystyrene, polyacrylates, polyvinyls, teflons, cotton, etc., may be preferred. A convenient nylon mesh which could be used in accordance with the invention is Nitex, a nylon filtration mesh having an average pore size of 210 µm and an average nylon fiber diameter of 90 µm (#3-210/36, Tetko, Inc., N.Y.).

Stromal cells comprising fibroblasts, mesenchymal stem cells liver reserve cells, neural stem cells, pancreatic stem cells and/or embryonic stem cells with or without other cells and elements described below, are inoculated onto the framework. Also, cells found in loose connective tissue may be inoculated onto the three-dimensional support along with fibroblasts. Such cells include but are not limited to smooth muscle cells, endothelial cells, pericytes, macrophages, monocytes, plasma cells, mast cells, adipocytes, etc. As previously explained, fetal fibroblasts can be used to form a "generic" three-dimensional stromal matrix that will support the growth of a variety of different cells and/or tissues. However, a "specific" stromal tissue may be prepared by inoculating the three-dimensional framework with fibroblasts derived from the same type of tissue to be cultured and/or from a particular individual who is later to receive the cells and/or tissues grown in culture in accordance with the three-dimensional system of the invention.

Thus, in one embodiment of the invention, stromal cells which are specialized for the particular tissue may be cultured. For example, stromal cells of hematopoietic tissue, including but not limited to fibroblasts, endothelial cells, macrophages/monocytes, adipocytes and reticular cells, could be used to form the three-dimensional subconfluent stroma for the long term culture of bone marrow in vitro. Hematopoietic stromal cells may be readily obtained from the "buffy coat" formed in bone marrow suspensions by centrifugation at low forces, e.g., 3000×g. In the stromal layer that makes up the inner wall of arteries, a high proportion of undifferentiated smooth muscle cells can be added to provide the protein elastic. Stromal cells of liver may include fibroblasts, Kupffer cells, and vascular and bile duct endothelial cells. Similarly, glial cells could be used as the stroma to support the proliferation of neurological cells and tissues; glial cells for this purpose can be obtained by trypsinization or collagenase digestion of embryonic or adult brain (Ponten and Westermark, 1980, in Federof, S. Hertz, L., eds, "Advances in Cellular Neurobiology," Vol. 1, New York, Academic Press, pp. 209-227). The growth of cells in the three-dimensional stromal cell culture may be further enhanced by adding to the framework, or coating the support with proteins (e.g., collagens, elastic fibers, reticular fibers) glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials.

Further, mesenchymal stem cells (lineage committed or uncommitted progenitor cells) are advantageous "stromal" cells for inoculation onto the framework. The cells may differentiate into osteocytes, fibroblasts of the tendons and ligaments, marrow stromal cells, adipocytes and other cells of connective tissue, chondrocytes, depending of course, on endogens or supplemented growth and regulatory factors and other factors including prostaglandin, interleukins and naturally-occurring chalones which regulate proliferation and/or differentiation.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to, the use of grinders, blenders, sieves, homogenizers, pressure cells, or insonators to name but a few. For a review of tissue disaggregation techniques, see Freshney, *Culture of Animal Cells: A Manual of Basic Technique,* 2d Ed., A.R. Liss, Inc., New York, 1987, Ch. 9, pp. 107-126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, *Culture of Animal Cells: A Manual of Basic Techniques,* 2d Ed., A.R. Liss, Inc., New York, 1987, Ch. 11 and 12, pp. 137-168.

The isolation of fibroblasts may, for example, be carried out as follows: fresh tissue samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional matrix (see, Naughton et al., 1987, *J. Med.* 18 (3 and 4) 219-250). Inoculation of the three-dimensional framework with a high concentration of stromal cells, e.g., approximately $10^6$ to $5 \times 10^7$ cells/ml, will result in the establishment of the three-dimensional stromal tissue in shorter periods of time.

After inoculation of the stromal cells, the three-dimensional framework should be incubated in an appropriate nutrient medium. As previously mentioned, many commercially available media such as RPMI 1640, Fisher's, Iscove's, McCoy's, and the like may be suitable for use. It is important that the three-dimensional stromal cell cultures be suspended or floated in the medium during the incubation period in order to maximize proliferative activity. The culture is "fed" periodically and the conditioned media of the invention is recovered and processed as described below in Sections 5.6 and 5.7. Thus, depending upon the tissue to be cultured and the collagen types desired, the appropriate stromal cell(s) may be selected to inoculate the three-dimensional matrix.

During incubation of the three-dimensional stromal cell cultures, proliferating cells may be released from the matrix. These released cells may stick to the walls of the culture vessel where they may continue to proliferate and form a confluent monolayer. This should be prevented or minimized, for example, by removal of the released cells during feeding, or by transferring the three-dimensional stromal culture to a new culture vessel. The presence of a confluent monolayer in the vessel will "shut down" the growth of cells in the three-dimensional matrix and/or culture. Removal of the confluent monolayer or transfer of the culture to fresh media in a new vessel will restore proliferative activity of the three-dimensional culture system. It should be noted that the conditioned media of the invention is processed, if necessary, so that it does not contain any whole cells (unless of course, whole cells are used for a specific application). Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the culture, so that they will not stick to the walls of the vessel and grow to confluence.

Other cells, such as parenchymal cells, may be inoculated and grown on the three-dimensional living stromal tissue.

Inoculation of Tissue-Specific Cells onto Three-Dimensional Stromal Matrix and Maintenance of Cultures Once the three-dimensional stromal cell culture has reached the appropriate degree of growth, additional cells such as tissue-specific cells (parenchymal cells) or surface layer cells which are desired to be cultured may also be inoculated onto the living stromal tissue. The cells are grown on the living stromal tissue in vitro to form a cultured counterpart of the native tissue and condition the media by elaborating extracellular products into the media at ratios resembling physiological levels. A high concentration of cells in the inoculum will advantageously result in increased proliferation in culture much sooner than will low concentrations. The cells chosen for inoculation will depend upon the tissue to be cultured, which may include, but is not limited to, bone marrow, skin, liver, pancreas, kidney, neurological tissue, adrenal gland, mucosal epithelium, and smooth muscle, to name but a few. Such cells with elaborate characteristic extracellular proteins such as certain growth factors into the media resulting in media optimized for certain tissue specific applications.

For example, and not by way of limitation, a variety of epithelial cells can be cultured on the three-dimensional living stromal tissue. Examples of such epithelial cells include, but are not limited to, keratinocytes, oral mucosa and gastrointestinal (G.I.) tract cells. Such epithelial cells may be isolated by enzymatic treatment of the tissue according to methods known in the art, followed by expansion of these cells in culture and application of epithelial cells to the three-dimensional stromal support cell matrix. The presence of the stromal support provides growth factors and other proteins which promote normal division and differentiation of epithelial cells.

In general, this inoculum should include the "stem" cell (also called the "reserve" cell) for that tissue; i.e., those cells which generate new cells that will mature into the specialized cells that form the various components of the tissue.

The parenchymal or other surface layer cells used in the inoculum may be obtained from cell suspensions prepared by disaggregating the desired tissue using standard techniques described for obtaining stromal cells in Section 5.3 above. The entire cellular suspension itself could be used to inoculate the three-dimensional living stromal tissue. As a result, the regenerative cells contained within the homogenate will proliferate, mature, and differentiate properly on the matrix, whereas non-regenerative cells will not. Alternatively, particular cell types may be isolated from appropriate fractions of the cellular suspension using standard techniques described for fractionating stromal cells in Section 5.1 above. Where the "stem" cells or "reserve" cells can be readily isolated, these may be used to preferentially inoculate the three-dimensional stromal support. For example, when culturing bone marrow, the three-dimensional stroma may be inoculated with bone marrow cells, either fresh or derived from a cryopreserved sample. When culturing skin, the three-dimensional stroma may be inoculated with melanocytes and keratinocytes. When culturing liver, the three-dimensional stroma may be inoculated with hepatocytes. When culturing pancreas, the three-dimensional stroma may be inoculated with pancreatic endocrine cells. For a review of methods which may be utilized to obtain parenchymal cells from various tissues, see, Freshney, Culture of Animal Cells. A Manual of Basic Technique, 2d Ed., A.R. Liss, Inc., New York, 1987, Ch. 20, pp. 257-288.

In fact, different proportions of the various types of collagen deposited on the stromal matrix prior to inoculation can affect the growth of the later-inoculated tissue-specific cells. For example, for optimal growth of hematopoietic cells, the matrix should preferably contain collagen types III, IV and I in an approximate ratio of 6:3:1 in the initial matrix. For three dimensional skin culture systems, collagen types I and III are preferably deposited in the initial matrix. The proportions of collagen types deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stromal cells used to inoculate the matrix can be a mixture of cells which synthesize the appropriate collagen type desired. The distribution and origins of various types of collagen is shown in Table I.

TABLE 1

DISTRIBUTIONS AND ORIGINS OF VARIOUS TYPES OF COLLAGEN

| Collagen Type | Principal Tissue Distribution | Cells of Origin |
| --- | --- | --- |
| I | Loose and dense ordinary connective tissue; collagen fibers | Fibroblasts and reticular cells; smooth |
|  | Fibrocartilage | muscle cells |
|  | Bone | Osteoblasts |
|  | Dentin | Odontoblasts |
| II | Hyaline and elastic cartilage | Chondrocytes |
|  | Vitreous body of eye | Retinal cells |
| III | Loose connective tissue; reticular fibers | Fibroblasts and reticular cells |
|  | Papillary layer of dermis |  |
|  | Blood vessels | Smooth muscle cells; endothelial cells |
| IV | Basement membranes | Epithelial and endothelial cells |
|  | Lens capsule of eye | Lens fibers |
| V | Fetal membranes; placenta | Fibroblast |
|  | Basement membranes |  |
|  | Bone |  |
|  | Smooth muscle | Smooth muscle cells |
|  | Fibroblasts |  |
| VI | Connective Tissue |  |
| VII | Epithelial basement membranes, anchoring fibrils | Fibroblasts, keratinocytes |
|  | Cornea | Corneal fibroblasts |
| VIII | Cartilage |  |
| IX | Hypertrophic cartilage |  |
| X | Cartilage | Fibroblasts |
| XI | Papillary dermis | Fibroblasts |
| XII | Reticular dermis | Fibroblasts |
| XIV | P 170 bullous pemphigoid antigen undulin | Keratinocytes |
| XVII |  |  |

During incubation, the three-dimensional cell culture system should be suspended or floated in the nutrient medium. Cultures should be fed with fresh media periodically. Again, care should be taken to prevent cells released from the culture from sticking to the walls of the vessel where they could proliferate and form a confluent monolayer. The release of cells from the three-dimensional culture appears to occur more readily when culturing diffuse tissues as opposed to structured tissues. For example, the three-dimensional skin culture of the invention is histologically and morphologically normal; the distinct dermal and epidermal layers do not release cells into the surrounding media. By contrast, the three-dimensional bone marrow cultures of the invention release mature non-adherent cells into the medium much the way such cells are released in marrow in vivo. As previously explained, should the released cells stick to the culture vessel and form a confluent monolayer, the proliferation of the three-dimensional culture will be "shut down". This can be avoided by removal of released cells during feeding, transfer of the three-dimensional culture to a new vessel, by agitation of the culture to prevent sticking of released cells to the vessel wall, or by the continuous flow of fresh media at a rate sufficient to replenish nutrients in the culture and remove released cells. As previously mentioned, the conditioned media is processed, if necessary, so that it is free of whole cells and cellular debris.

The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

Genetically Engineered Constructs

In another embodiment, the three-dimensional constructs conditioning the media can act as vehicles for introducing gene products into the media that promote the repair and/or regeneration of tissue defects, for example. The cells can be genetically engineered to express, for example, inflammatory mediators, such as IL-6, IL-8 and G-CSF. The cells could also or alternatively be genetically engineering to express anti-inflammatory factors, e.g., anti-GM-CSF, anti-TNF, anti-IL-1, anti-IL-2, etc.

In another embodiment, the cells can be genetically engineered to express a gene into the media which would exert a therapeutic effect, e.g., in the production of TGF—to stimulate cartilage production, or other factors such as BMP-13 to promote chondrogenesis or stimulatory factors that promote migration of stromal cells and/or matrix deposition. Since the constructs comprise eukaryotic cells, the gene product will be properly expressed and processed to form an active product. Preferably, the expression control elements used should allow for the regulated expression of the gene so that the product can be over-synthesized in culture. The transcriptional promoter chosen, generally, and promoter elements specifically, depend, in part, upon the type of tissue and cells cultured. Cells and tissues which are capable of secreting proteins are preferable (e.g., those having abundant rough endoplasmic reticulum and Golgi complex organelles). The over-produced gene product will then be secreted by the engineered cell into the conditioned media.

The cells used to condition the media may be genetically engineered to regulate one or more genes; or the regulation of gene expression may be transient or long-term; or the gene activity may be non-inducible or inducible.

The cells that condition the media can also be genetically engineered to "knock out" expression of factors that promote inflammation. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to the cell can be reduced or knocked out using a number of techniques, for example, expression may be inhibited by inactivating the gene completely (commonly termed "knockout") using standard homologous recombination techniques. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion or an inactivating insertion in part of a gene, or by deleting the entire gene. By using a construct with two regions of homology to the target gene that are far apart in the genome, the sequences intervening the two regions can be deleted. Mombaerts et al., 1991, *Proc. Nat. Acad. Sci. USA*. 88:3084-3087. Alternatively, a gene may also be inactivated by deletion of upstream or downstream expression elements.

Antisense and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Furthermore, appropriate ribozyme molecules can be designed as described, e.g., by Haseloff et al., 1988, *Nature* 334:585-591; Zaug et al., 1984, *Science* 224: 574-578; and Zaug and Cech, 1986, *Science* 231:470-475. Still further, triple helix molecules can be utilized in reducing the level of target gene activity. These techniques are described in detail by L. G. Davis et al., eds, *Basic Methods in Molecular Biology*, 2nd ed., Appleton & Lange, Norwalk, Conn. 1994.

Methods that may be useful to genetically engineer the cells of the invention are well-known in the art and are further detailed in co-owned U.S. Pat. Nos. 4,963,489 and 5,785,964, the disclosures of which are incorporated herein by reference. For example, a recombinant DNA construct or vector containing an exogenous nucleic acid, e.g., encoding a gene product of interest, may be constructed and used to transform or transfect the stromal cells of the invention. Such transformed or transfected cells that carry the exogenous nucleic acid, and that are capable of expressing said nucleic acid, are selected and clonally expanded in the three-dimensional constructs of this invention.

Methods for preparing DNA constructs containing the gene of interest, for transforming or transfecting cells, and for selecting cells carrying and expressing the gene of interest are well-known in the art. See, for example, the techniques described in Maniatis et al., 1989, *Molecular Cloning, A Laboratory Manual*, Cold Spring Harbor Laboratory Press, Cold Spring Harbor, N.Y.; Ausubel et al., 1989, *Current Protocols in Molecular Biology*, Greene Publishing Associates & Wiley Interscience, N.Y.; and Sambrook et al., 1989, *Molecular Cloning: A Laboratory Manual*, 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adena-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors may be preferred, since either inducible or constitutive promoters can be used in these systems to control expression of the gene of interest. Alternatively, integrating vectors can be used to obtain transient expression, provided the gene of interest is controlled by an inducible promoter.

Other methods of introducing DNA into cells include the use of liposomes, lipofection, electroporation, a particle gun, or by direct DNA injection.

The cells are preferably transformed or transfected with a nucleic acid, e.g., DNA, controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines which express the gene product into the media.

Any promoter may be used to drive the expression of the inserted gene. For example, viral promoters include but are not limited to the CMV promoter/enhancer, SV40, papillomavirus, Epstein-Barr virus, elastin gene promoter and -globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

According to one embodiment, the inducible promoters used for expressing exogenous genes of interest are those that are the native promoters of those regulatory proteins as disclosed herein that are induced as a result of cyropreservation and subsequent thawing. For example, the promoter of TGF-β, VEGF, or various known heat shock proteins can be used as the expression control element, i.e., can be operatively linked to an exogenous gene of interest in order to express a desired gene product in the tissue constructs conditioning the cell media.

A variety of methods may be used to obtain the constitutive or transient expression of gene products engineered into the cells. For example, the transkaryotic implantation technique described by Seldon et al., 1987, *Science* 236: 714-718 can be used. "Transkaryotic", as used herein, suggests that the nuclei of the implanted cells have been altered by the addition of DNA sequences by stable or transient transfection. Preferably, the cells are engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, fused to the gene product as the extracellular domain.

Furthermore, it may be desirable to prepare a construct having an extracellular matrix containing a foreign gene product, growth factor, regulatory factor, etc., which is then found in the conditioned media. This embodiment is based on the discovery that, during the growth of human stromal cells on a three-dimensional support framework, the cells synthesize and deposit on the framework a human extracellular matrix as produced in normal human tissue. The extracellular matrix is secreted locally by cells and not only binds cells and tissue together but also influences the development and behavior of the cells it contacts. The extracellular matrix contains various connective tissue proteins, e.g., fiber-forming proteins interwoven in a hydrated gel composed of a network of glycosaminoglycans chains. The glycosaminoglycans are a heterogeneous group of long, negatively charged polysaccharide chains, which (except for hyaluronic acid) are covalently linked to protein to form proteoglycans molecules. According to this embodiment of the invention, the stromal cells may be genetically engineered to express a desired gene product, or altered forms of a gene product, which will be present in the extracellular matrix and ultimately the cell medium.

Recovery of the Conditioned Media

The cells can be cultured by any means known in the art. Preferably, the cells are cultured in an environment which enables aseptic processing and handling. Conventional means of cell and tissue culture have been limited by the need for human supervision and control of the media. This limits the amount of cells and tissue that can be cultured at a single time and consequently the volume of conditioned cell media that can be obtained at a single time. For this reason, it is preferred that the media be conditioned in a manner allowing for large scale growth (yielding large scale conditioned media) using, for example, an apparatus for aseptic large scale culturing like that described in co-owned U.S. Pat. No. 5,763,267 (the '267 patent) which is incorporated by reference herein in its entirety for all purposes. Using the aseptic closed system described in the '267 patent, preconditioned culture media is transported from a fluid reservoir to an inlet manifold and evenly distributed to the cultures in a continuous flow system and is useful in culturing three-dimensional cell and tissue cultures, such as Dermagraft® for example. In particular, the apparatus described in the '267 patent includes a plurality of flexible or semi-flexible treatment chambers comprising one or more individual culture pockets, a plurality of rigid spacers, an inlet fluid manifold, an outlet fluid manifold, a fluid reservoir, and a means for transporting fluid within the system.

During treatment, liquid medium is transported from the fluid reservoir to the inlet manifold, which in turn evenly distributes the media to each of the connected treatment chambers and internal culture pockets. An outlet fluid manifold is also provided to ensure that each treatment chamber is evenly filled and to ensure that any air bubbles formed during treatment are removed from the treatment chambers. The treatment chambers are flexible or semi-flexible so as to provide for easy end-user handling during rinsing and application of the cultured transplants. Due to the flexibility of the treatment chambers, rigid spacers are also provided which ensure even fluid distribution within the chambers during treatment. When appropriate (i.e., once the medium is conditioned so that extracellular proteins such as growth factors have reached desirable levels in the medium) the "condition" medium is pumped out of the system and processed for use. Preferably, the conditioned cell medium is harvested from the apparatus at the later stages of growth of the tissue when the level of certain growth factors and connective tissue protein secretion is at its highest level (See FIG. 1). In a preferred embodiment, the medium conditioned by the three dimensional cell culture is collected after exposure of the medium to the cells at days 10 through day 14 of culturing.

In another embodiment, the three-dimensional tissue is cultivated in an apparatus for aseptic growth of three-dimensional tissue cultures as described in U.S. Pat. No. 5,843,766 (the '766 patent) incorporated herein in its entirety for all purposes. The '766 patent discloses a tissue culture chamber in which the chamber is a casing that provides for growth of three-dimensional tissue that can be grown, preserved in frozen form, and shipped to the end user in the same aseptic container. The tissue culture chamber includes a casing comprising a substrate within the casing designed to facilitate three-dimensional tissue growth on the surface of the substrate. The casing includes an inlet and an outlet port which assist the inflow and outflow of medium. The casing also includes at least one flow distributor. In one embodiment, the flow distributor is a baffle, which is used to distribute the flow of the medium within the chamber to create a continuous, uniform piece of three-dimensional tissue. In a second embodiment, the flow distributor is a combination of deflector plates, distribution channels, and a flow channel. In each embodiment, the casing further includes a seal so as to ensure an aseptic environment inside the chamber during tissue growth and storage. Again the medium is preferably harvested from the apparatus at the later stages of growth of the tissue when the level of in growth factors and connective tissue protein secretion is at its highest level (See FIG. 1). In a preferred embodiment, the medium conditioned by the three dimensional cell culture is collected after exposure of the medium to the cells at days 10 through day 14 of culturing.

Concentration of the Conditioned Medium

Following removal of the cell conditioned medium, it may be necessary to further process the resulting supernatant. Such processing may include, but are not limited to, concentration by a water flux filtration device or by defiltration using the methods described in *Cell & Tissue Culture: Laboratory Procedures*, supra, pp 29 D:0.1-29D:0.4.

Additionally, the medium may be concentrated 10 to 20 fold using a positive pressure concentration device having a filter with a 10,000 ml cut-off (Amicon, Beverly, Mass.).

Also, the conditioned medium may be further processed for product isolation and purification to remove unwanted proteases, for example. The methods used for product isolation and purification so that optimal biological activity is maintained will be readily apparent to one of ordinary skill in the art. For example, it may be desirous to purify a growth factor, regulatory factor, peptide hormone, antibody, etc. Such methods include, but are not limited to, gel chromatography (using matrices such as sephadex) ion exchange, metal chelate affinity chromatography with an insoluble matrix such as cross-linked agarose, HPLC purification and hydrophobic interaction chromatography of the conditioned media. Such techniques are described in greater detail in *Cell & Tissue Culture: Laboratory Procedures*, supra. Of course, depending upon the desired application of the conditioned medium, and/or products derived thereof, appropriate measures must be taken to maintain sterility. Alternatively, sterilization may be necessary and can be accomplished by methods known to one of ordinary skill in the art, such as, for example, heat and/or filter sterilization taking care to preserve the desired biological activity.

Isolation of Collagen

Figure 4:
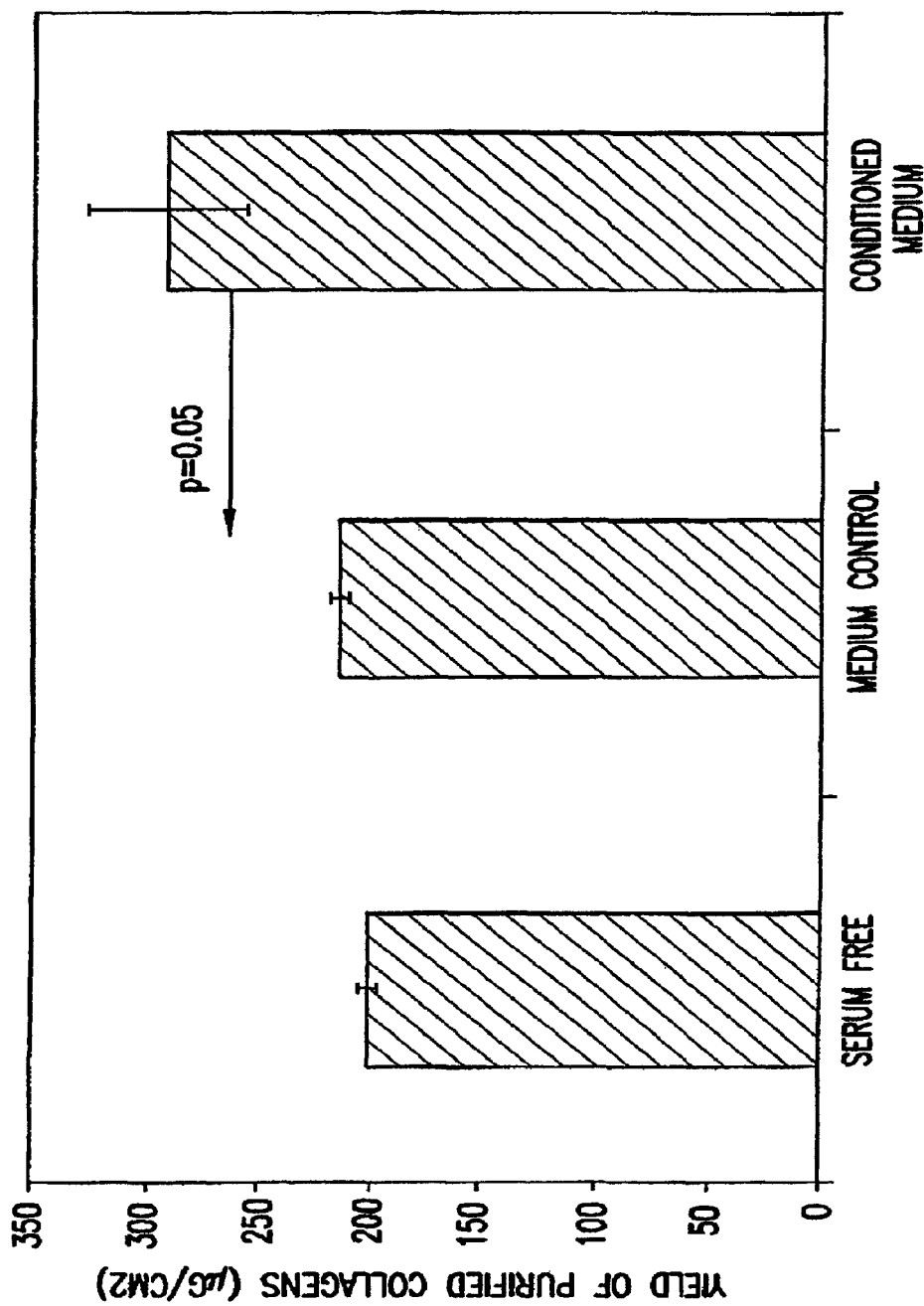
FIG. 4 is a graph representing the effect of 1× conditioned medium (cell culture medium which has previously supported the growth of cells in Transcyte™) on collagen deposition of cells grown in three dimensions in comparison to base medium DMEM (containing 10% BLS supplemented medium with 2 mM L-glutamine and 1× antibiotic/antimycotic) supplemented with a 1× final concentration of serum-free medium and medium. A statistically significant ($p=0.05$) increase of almost 50% was noted in collagen deposition of cultures treated with the conditioned medium for 10 days as compared with either control.

As previously mentioned, the conditioned medium of the invention contains numerous products which may be isolated and purified therefrom. For example, human dermal fibroblasts synthesize and secrete collagen precursors and a fraction of these precursors are incorporated into a three-dimensional extracellular matrix. This incorporation requires the removal of terminal peptides (N- and C-peptides) which significantly lowers the solubility of the collagen molecules (the rest of the secreted collagen remains in solution due to lack of proteolysis). Generally, soluble collagen may be obtained under neutral pH conditions at high salt concentrations. See Kielty, C. M., I. Hopkinson, et al. (1993), *Collagen: The Collagen Family: Structure, Assembly, and Organization in the Extracellular Matrix, Connective Tissue and Its Heritable Disorders: molecular, genetic and medical aspects*. P. M. Royce and B. Steinmann. New York, Wiley-Liss, Inc.: 103-149). Applicants provide data showing the effect of conditioned medium (medium which has previously supported the growth of cells cultured in three dimensions) on the preparation and composition of three-dimensional tissues by measuring the amount of collagen secreted into the extracellular matrix of tissues cultured in the presence of serum-free medium, medium or three dimensional conditioned medium (see Section 6.3). The conditioned medium of the invention significantly increases collagen deposition of tissue in vitro as shown in FIG. 4.

Further, Applicants' have discovered that, surprisingly, collagen is not laid down in linear fashion, but is instead secreted at increasing levels during the culturing process (see FIG. 1). Accordingly, Applicants' have applied this discovery when harvesting the collagen.

It should be understood that the following protocol is offered by way of example and may be modified using methods known to those of skill in the relevant art. To purify the collagen, add 240 mL of medium conditioned with fibroblasts to 240 mL 5M NaCl (a 1:1 ratio of medium to salt) and precipitate for 16 hours at 4° Celsius. Centrifuge the suspension for approximately 20 minutes at 4000×g. Discard the supernatant. Wash the pellet with 10 mL of a solution of 50 mM Tris-HCl (pH 7.5) and 2.4M NaCl. Centrifuge for 20 minutes at 4000×g and discard the supernatant. Resuspend the pellet in 10 mL of 0.5M acetic acid. To remove the propeptides, add 0.1 mL of pepsin (100 mg/mL) (Sigma Chemical, St. Louis, Mo.) and digest for 16 hours at 4° Celsius (this removes the propeptides but leaves the triple helix intact). Centrifuge the suspension for 20 minutes at 4000×g. Recover supernatant and discard the pellet. Add 2.1 mL of 5M NaCl and 0.5M acetic acid to a final volume of 15 mL (final NaCl concentration of 0.7M). Precipitate for approximately 16 hours at 4° Celsius. Centrifuge the suspension for 20 minutes at 4000×g and discard the supernatant. Dissolve pellet in 0.5 mL of 0.5M acetic acid solution. The purity of the collagen should be at least 90% and may be analyzed by standard methods known in the art such as SDS-PAGE, for example.

Applications Using the Conditioned Media

Wound Healing Applications

The conditioned media of the invention may be processed to promote wound and burn healing. When tissue is injured, polypeptide growth factors, which exhibit an array of biological activities, are released into the wound to promote healing. Wound healing is a complex process that involves several stages and is capable of sealing breaches to the integument in a controlled manner to form functionally competent tissue. The process begins with hemostasis followed by an inflammatory phase involving neutrophils and macrophages. The process continues with the development of granulation tissue and re-epithelialization to close the wound. Subsequently, scar tissue forms and is remodeled over the succeeding months to an approximation of the original anatomical structure. Ideally, scar tissue is minimal so that healthy tissue, functionally competent tissue which histologically and physiologically resembles the original normal tissue, may form.

Each stage of the healing process is controlled by cellular interactions through regulatory proteins such as cytokines, growth factors, and inflammatory mediators as well as cell contact mechanisms. For example, inflammatory mediators such as IL-6, IL-8, and G-CSF induce lymphocyte differentiation and acute phase proteins, as well as neutrophil infiltration, maturation and activation, processes that are important in the inflammatory stages of wound healing. Other examples of regulatory proteins involved in the wound healing process are VEGF that induces angiogenesis during inflammation and granulation tissue formation, the BMP's which induce bone formation, KGF that activates keratinocytes and TGF-β1 that induces deposition of extracellular matrix. Table 2 (below) lists the concentration of a number of growth factors determined by ELISA (enzyme linked immuno assay) to be in Applicants' conditioned medium which previously supported the growth of the cells grown in Dermagraft® tissue culture. It should be understood that the following list is not an all inclusive list of factors and is provided solely to further characterize the conditioned medium by providing the concentration of some of the biologically active factors present in the medium of the invention.

TABLE 2

Growth Factor Concentrations in Conditioned Medium as Measured by ELISA

| VEGF | 3.2 ng/ml |
|---|---|
| G-CSF | 2.3 ng/ml |
| IL-8 | 0.9 ng/ml |
| IL-8 | 3.2 ng/ml |
| KGF | 1.67 ng/ml |
| TGF-β | 0.8 ng/ml |

In chronic wounds, the healing process is interrupted at a point subsequent to hemostasis and prior to re-epithelialization, and is apparently unable to restart. Most of the inflammation seen in the wound bed is related to infection, but the inflammation gives rise to an environment rich in proteases that degrade regulatory proteins and thus interfere with the wound healing process.

Figure 2:
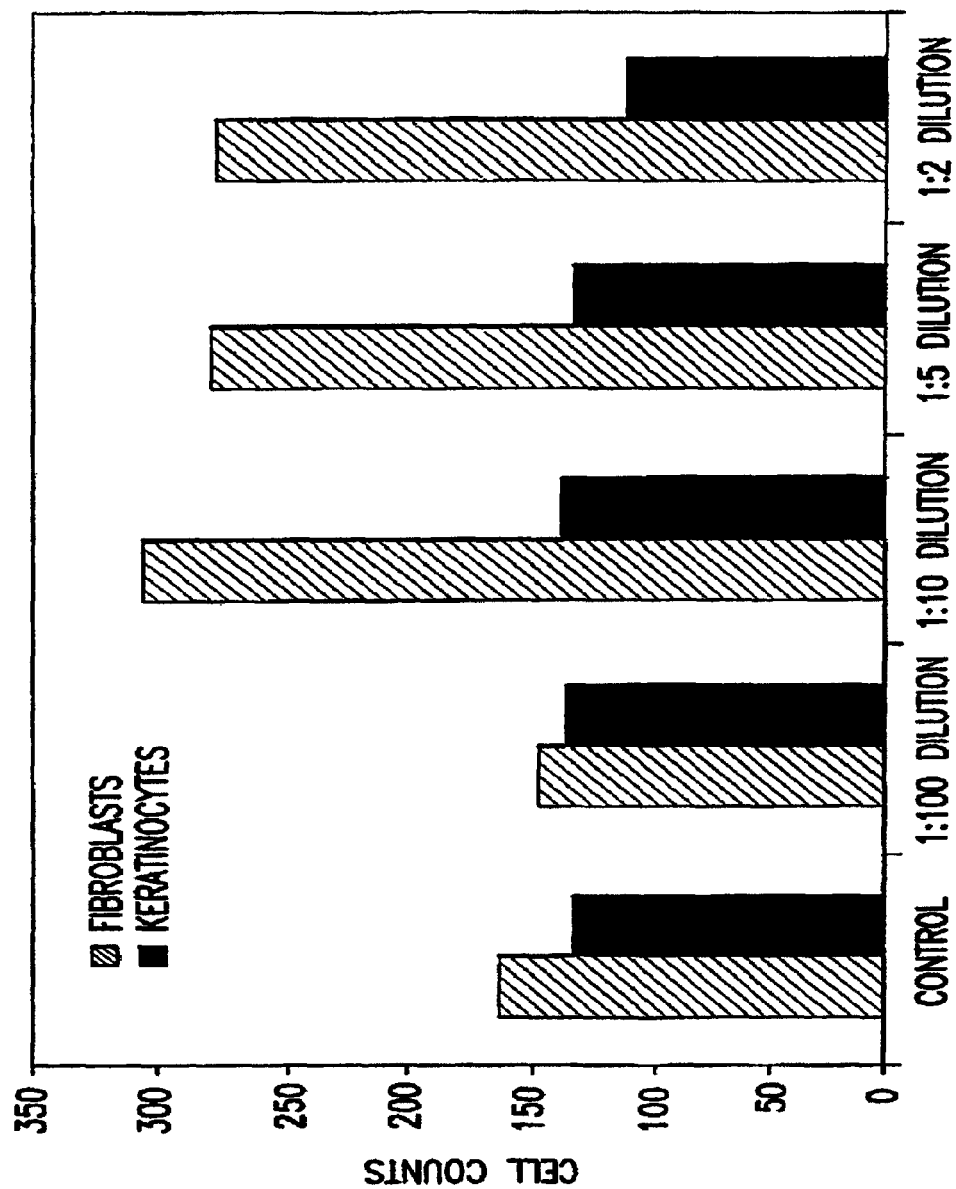
FIG. 2 is a graph representing the effect of extracellular matrix (removed from Transcyte™) and added at dilutions of 1:2, 1:5, 1:10, and 1:100 to monolayer cultures of human fibroblasts and keratinocytes. The most significant effect illustrated is at a 1:10 dilution of the matrix.

A variety of methods have been utilized to quantify and characterize the major molecular components secreted by fibroblasts found in the three-dimensional tissue cultures TransCyte™ and Dermagraft®). The human matrix proteins and glycosaminoglycans (GAGs) present in TransCyte™ and Dermagraft® include, but are not limited to, collagen I, III, fibronectin, tenascin, decorin, versican betaglycan, syndecan as well as other components (data not shown). These secreted proteins and GAGs serve major structural functions as well as stimulate cell division, migration, adhesion and signal transduction. The deposition of glycosaminoglycans (deposition volume is dependent on period of growth) and collagen (deposition volume is not dependent on period of growth) in the three-dimensional growth systems are illustrated in FIG. 1. The components have been measured by ELISA, Western blot analysis, immuno histochemistry and PCR. For example, some of the components found in TransCyte™ include collagen I, III, and VII (RNA), fibronectin, tenascin, thrombospondin 2, elastin, proteoglycans, decorin, versican as well as other components (data not shown). Activity of these components in tissue development, healing, and normal function have been well described. Additionally, Applicants describe certain effects of the human bioengineered matrix on cell function in vitro. For example, Applicants have noted that cell proliferation is increased by adding bioengineered matrix. To study its effects on cell proliferation, matrix was physically removed from TransCyte™ and Dermagraft® and added in varying dilutions to monolayer cultures of human fibroblasts and keratinocytes. The results of increased cell proliferation are shown in FIG. 2.

Further, as detailed in section 6.3, Applicants note the effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium. The effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium. The conditioned medium of the invention significantly increases collagen deposition of tissue in vitro as shown in FIG. 4. As the present invention contains many of the regulatory proteins thought to be important in wound healing and which have been shown to be depleted in in vivo models of wound healing. Furthermore, in some medical conditions, such as diabetes, some of the regulatory proteins needed for wound healing are in short supply. For example, it has been found in a mouse model of non-insulin-dependent diabetes (e.g., the db/db mouse) that secretion of VEGF and PDGF and expression of the PDGF receptor are all depressed in wounds compared to the levels in wounds of normal mice.

Also, the conditioned media provided by the present invention is also useful in the treatment of other types of tissue damage, e.g., traumatic or congenital, wherein the repair and/or regeneration of tissue defects or damage is desired since many of these growth factors are found in Applicants' conditioned cell media, including, for example, fibroblast growth factors (FGFs), platelet derived growth factors (PDGFs), epidermal growth factors (EGFs), bone morphogenetic proteins (BMPs) and transforming growth factors (TGFs); as well as those which modulate vascularization, such as vascular endothelial growth factor (VEGF), keratinocyte growth factor (KGF), and basic FGF; angiogenesis factors, and antiangiogenesis factors. Stress proteins, such as GR 78 and MSP90 induce growth factors such as TGF-$\beta$. TGF-$\beta$, including TGF $\beta$-1, TGF $\beta$-2, TGF $\beta$-3, TGF $\beta$-4 and TGF $\beta$-5, regulate growth and differentiation and accelerate wound healing (Noda et al. 1989, Endocrin. 124: 2991-2995; Goey et al. 1989, *J. Immunol.* 143: 877-880, Mutoe et al. 1987, *Science* 237: 1333-1335). Mitogens, such as PDGF increase the rate of cellularity and granulation in tissue formation (Kohler et al. 1974, *Exp. Cell. Res.* 87: 297-301). As previously mentioned, the cells are preferably human to minimize immunogenicity problems.

Figure 3:
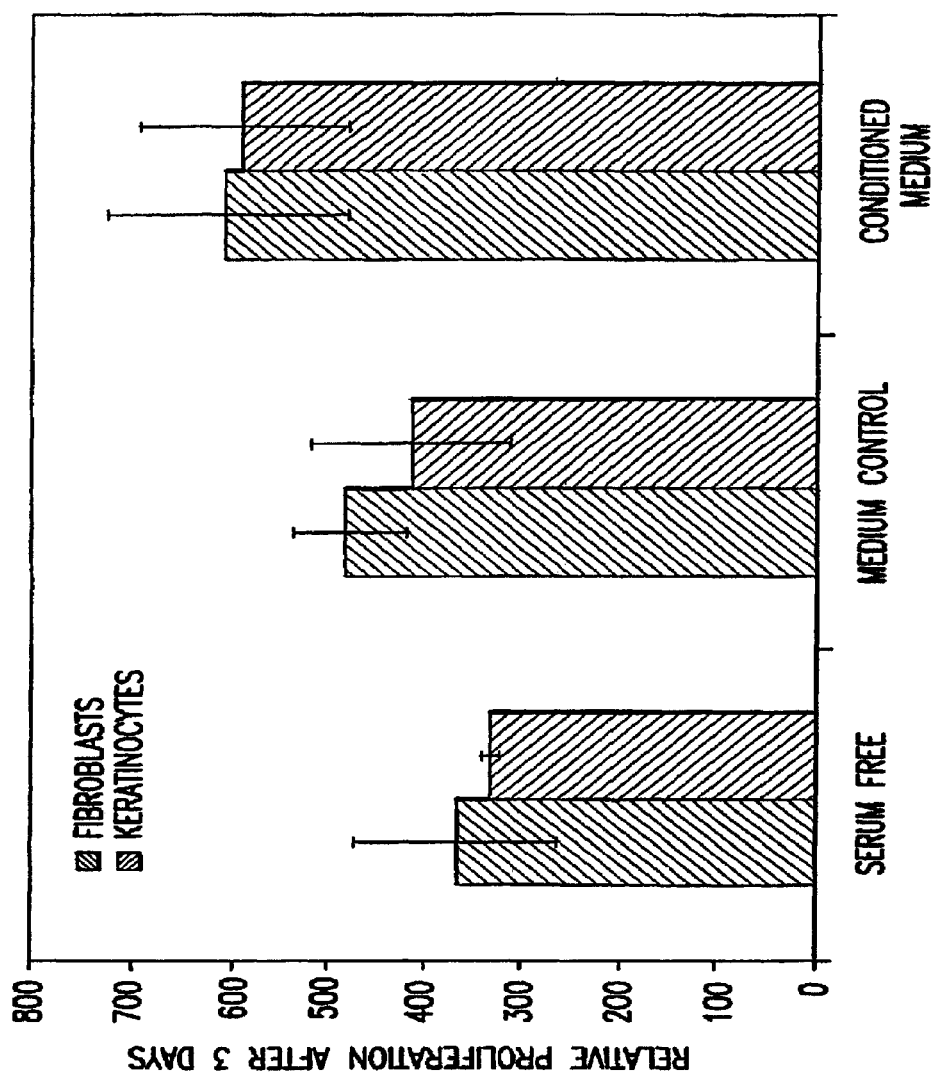
FIG. 3 is a graph representing relative proliferation of human fibroblasts and keratinocytes exposed to conditioned medium (cell culture medium which has previously supported the growth of cells in Transcyte™). An increase in cell response was revealed in as little as three days.

Because the conditioned media of the invention contains such an array of wound healing factors, the conditioned media is advantageously used in the treatment of wound and burn healing including skin wounds, broken bones, gastric ulcers, pancreas, liver, kidney, spleen, blood vessel injuries and other internal wounds. Further, the conditioned media may be combined with other medicinal ingredients such as antibiotics and analgesics. Embodiments include formulations of the conditioned media with a salve or ointment for topical applications. In fact, the conditioned medium of the invention has been shown to induce proliferation of human fibroblasts and keratinocytes. An increase in cell response was noted by cells exposed to the conditioned medium in as little as 3 days in vitro (FIG. 3).

Alternatively, the conditioned medium may be combined with a bandage (adhesive or non-adhesive) to promote and/or accelerate wound healing. The conditioned media may be used in any state, i.e., liquid or solid, frozen lyophilized or dried into a powder, as a film for topical wound treatments and anti-adhesion applications, as an injectable, see PCT WO 96/39101, incorporated herein by reference it its entirety.

Alternatively, the conditioned cell medium of the present invention may be formulated with polymerizable or cross-linking hydrogels as described in U.S. Pat. Nos. 5,709,854; 5,516,532; 5,654,381; and WO 98/52543, each of which is incorporated herein by reference in its entirety. Examples of materials which can be used to form a hydrogel include modified alginates. Alginate is a carbohydrate polymer isolated from seaweed, which can be cross-linked to form a hydrogel by exposure to a divalent cation such as calcium, as described, for example in WO 94/25080, the disclosure of which is incorporated herein by reference. Alginate is ionically cross-linked in the presence of divalent cations, in water, at room temperature, to form a hydrogel matrix. As used herein, the term "modified alginates" refers to chemically modified alginates with modified hydrogel properties.

Additionally, polysaccharides which gel by exposure to monovalent cations, including bacterial polysaccharides, such as gellan gum, and plant polysaccharides, such as carrageenans, may be cross-linked to form a hydrogel using methods analogous to those available for the cross-linking of alginates described above.

Modified hyaluronic acid derivatives are particularly useful. As used herein, the term "hyaluronic acids" refers to natural and chemically modified hyaluronic acids. Modified hyaluronic acids may be designed and synthesized with preselected chemical modifications to adjust the rate and degree of cross-linking and biodegradation.

Covalently cross-linkable hydrogel precursors also are useful. For example, a water soluble polyamine, such as chitosan, can be cross-linked with a water soluble diisothiocyanate, such as polyethylene glycol diisothiocyanate.

Alternatively, polymers may be utilized which include substituents which are cross-linked by a radical reaction upon contact with a radical initiator. For example, polymers including ethylenically unsaturated groups which can be photochemically cross-linked which may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically cross-linked may be utilized, as disclosed in Matsuda et al., *ASAID Trans.*, 38: 154-157 (1992).

The preferred polymerizable groups are acrylates, diacrylates, oligoacrylates, dimethacrylates, oligomethacrylates, and other biologically acceptable photopolymerizable groups. Acrylates are the most preferred active species polymerizable group.

Naturally occurring and synthetic polymers may be modified using chemical reactions available in the art and described, for example, in March, "Advanced Organic Chemistry", 4th Edition, 1992, Wiley-Interscience Publication, New York.

Polymerization is preferably initiated using photo initiators. Useful photo initiators are those which can be used to initiate polymerization of the macromers without cytotoxicity and within a short time frame, minutes at most and most preferably seconds.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanolamine, trithylamine, dibenzyl amine, N-benzylethanolamine, -isopropyl benzylamine. Triethanolamine is a preferred cocatalyst.

In another embodiment, the conditioned media of the invention, or alternatively particular extracellular matrix proteins elaborated into the media, are used to provide an excellent substance to coat sutures. The naturally secreted extracellular matrix provides the conditioned media with type I and type III collagens, fibronectin, terascin, glycosaminologycans, acid and basic FGF, TGF-α and TGF-β, KGF, versican, decorin and various other secreted human dermal matrix proteins. Similarly, the conditioned cell media of the invention or the extracellular matrix proteins derived from the conditioned media may be used to coat conventional implantation devices, including vascular prosthesis, in surgical approaches to correct defects in the body-resulting in superior implantation devices. The implants should be made of biocompatible, inert materials that replace or substitute for the defective function and made of either non-biodegradable materials or biodegradable materials. By coating implantation devices with the medium containing these extracellular proteins, the implant invites proper cellular attachments resulting in superior tissue at the implantation site. Thus, sutures, bandages, and implants coated with conditioned cell media, or proteins derived from the media, enhance the recruitment of cells, such as leukocytes and fibroblasts into the injured area and induce cell proliferation and differentiation resulting in improved wound healing.

In another embodiment, the conditioned medium may be formulated with a pharmaceutically acceptable carrier as a vehicle for internal administration. Also, the medium may be further processed to concentrate or reduce one or more factor or component contained within the medium, for example, enrichment of a growth factor using immunoaffinity chromatography or, conversely, removal of a less desirable component, for any given application as described herein.

Of course, wounds at specialized tissues may require medium conditioned by that specialized tissue. For example, injuries to neuronal tissues may require proteins contained in medium conditioned by neuronal cell cultures. Specific products may be derived, or alternatively, the conditioned medium may be enriched by immunoaffinity chromatography or enhanced expression of a desired protein from the specific medium such as, for example, NGF. NGF-controlled features include, but are not limited to, the cholinergic neurotransmitter function (acetylcholinesterase (AChE) and the acetylcholine-synthesizing enzyme (ChAT)), neuronal cell size, and expression of Type II NGF receptors; NGF is secreted into the conditioned medium conditioned by glial and other neuronal cells cultured on a three-dimensional stromal tissue, which can then be used in a composition for nerve healing.

Deficits of endogenous NGF aggravate certain human neurodegenerative disorders and there is an apparent inability of injured adult CNS neurons to regenerate. Specifically, injury to a nerve is followed by degeneration of the nerve fibers distal to the injury, the result of isolation of the axon from the cell body. In the central nervous system, there is no significant growth at the site of injury typically leading to death of the damaged neuron. NGF plays a crucial role in the regenerative capabilities of adult CNS cholinergic neurons at the cell body level (e.g., septum), the intervening tissue spaces (e.g., nerve bridge) and the reinervation area (e.g., hippocampal formation). Additionally, NGF may be beneficial in improving cognitive defects. Medium conditioned with glial cells for example, can supply exogenous NGF and other nerve growth factors so that new axons can grow out from the cut ends of the injured nerve (e.g., develop a growth cone) elongating to the original site of the connection.

Further, injury to the brain and spinal cord is often accompanied by a glial response to the concomitant axonal degeneration, resulting in scar tissue. This scar tissue was initially thought to be a physical barrier to nerve growth, however, of greater significance is the presence or absence of neuronotropic factors in the extra neuronal environment. Astrocytes appear to be capable of synthesizing laminin in response to injury (laminin can also be found in the conditioned media as discussed in greater detail in Section 5.8.2 relating to extracellular matrix proteins). Collagen and fibronectin, and especially laminin, have been found to promote the growth of neurities from cultured neurons or neuronal explants in vitro. These extracellular matrix proteins appear to provide an adhesive substratum which facilitates the forward movement of the growth cone and elongation of the axon. Thus, the presence of neuronotropic factors and a supportive substratum are required for successful nerve regeneration since regeneration appears to require that: the neuronal cell body be capable of mounting the appropriate biosynthetic response; and the environment surrounding the injury site be capable of supporting the elongation and eventual functional reconnection of the axon. Medium conditioned by nerve cells such as astrocytes and glial cells contains the neuronotropic growth factors and extracellular matrix proteins necessary for nerve regeneration in brain and spinal cord injuries. Thus, in one embodiment, the conditioned medium is formulated for the treatment of such injuries.

In other embodiments, the treatment of skin, bones, liver, pancreas, cartilage, and other specialized tissues may be treated with media conditioned by their respective specialized cell types, preferably cultured in three-dimensions, resulting in a conditioned medium containing characteristic extracellular proteins and other metabolites of that tissue type useful for treating wounds to that respective tissue type.

The conditioned cell medium may also be added to devices used in periodontal surgery in order to promote uniform tissue repair, to provide biodegradable contact lenses, corneal shields or bone grafts, to provide surgical space fillers, to promote soft tissue augmentation, particularly in the skin for the purpose of reducing skin wrinkles, and as urinary sphincter augmentation, for the purpose of controlling incontinence.

In another embodiment, the compositions may be lyophilized/freeze-dried and added as a wound filler (e.g., fill holes left from hair plugs for implantation) or added to existing wound filling compositions to accelerate wound healing. In another embodiment, the medium is conditioned with genetically engineered cells to increase the concentration of wound healing proteins in the medium. For example, the cells may be engineered to express gene products such as any of the growth factors listed above.

The Repair and Correction of Congenital Anomalies, Acquired Defects and Cosmetic Defects The medium compositions may also be used to repair and correct a variety of anomalies, both congenital and acquired as well as cosmetic defects, both superficial and invasive. For example, the compositions may be added in any form and may be used in a hydrogel, injectable, cream, ointment, and may even be added to eye shadow, pancake makeup, compacts or other cosmetics to fortify the skin topically.

In another embodiment, topical or application by any known method such as injection, oral, etc., of the conditioned medium is made to reverse and/or prevent wrinkles and a number of the deleterious effects induced by UV light, exposure to a variety of pollutants and normal aging for example.

Additionally, in another embodiment, the medium of the invention is used to reduce cell aging and the inhibit the activity of the factors which cause skin cancer. That the conditioned medium has antioxidant activity is shown in Section 7.1. Again, application to a mammal may be topical or application by any known method such as injection, oral, etc. Applicants have discovered that a statistically significant ($p<0.003$) reduction in intracellular oxidation of approximately 50 percent was noted in human keratinocytes exposed to Applicants' conditioned medium.

Figure 5:
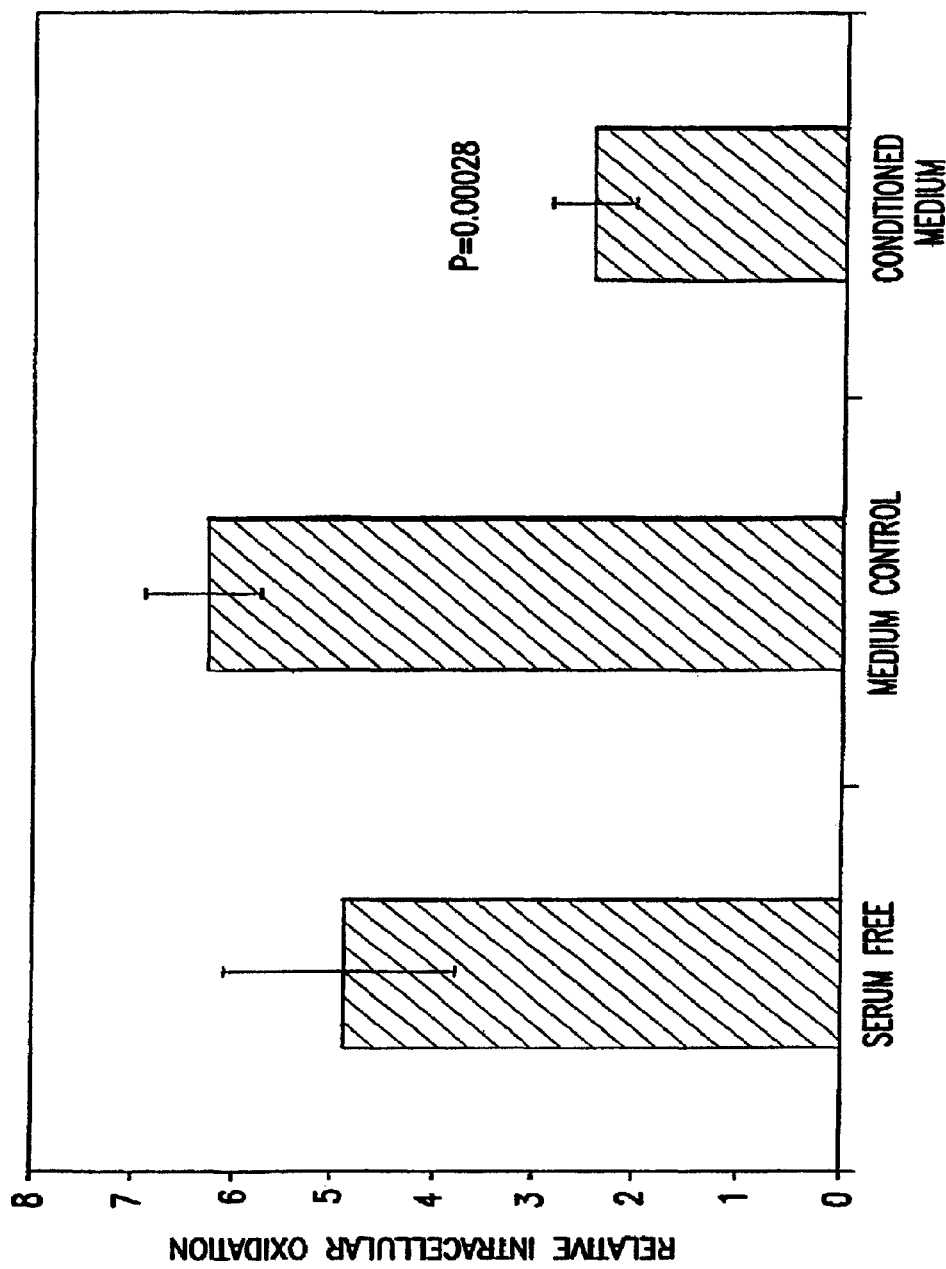
FIG. 5 is a graph representing the anti-oxidant activity in conditioned cell medium (cell culture medium which has previously supported the growth of cells in Transcyte™) on human epidermal keratinocytes in culture. A statistically significant ($p<0.0003$) reduction in intracellular oxidation of approximately 50% was noted in human keratinocytes exposed to conditioned medium which had previously supported Transcyte™ for three days.

Thus, in addition to inducing epidermal and dermal cell proliferation and collagen secretion in vitro the conditioned medium of the invention has strong antioxidant activity (FIG. 5). Also, the factors are relatively stable and TGF $\beta$, VEGF, and collagen content were stable after 21 days storage at 37° C. at pH 7.4 and 5.5. Solutions stored 2+ years at −20° C. maintained stable levels of TGF $\beta$1 and VEGF.

This sterile enriched nutrient solution represents a bioengineered cosmeceutical that is readily available in large volumes and may be useful as an additive for a variety of skin, cosmetic, and dermatologic products to supplement the levels of growth factors and matrix molecules in human skin, hair, and nails. Products are envisioned to use with Alpha Hydroxy Acids exfoliates to potentially optimize penetration of the growth factors and other biomolecules into the skin and with chemical peels to potentially accelerate healing and reduce inflammation.

The conditioned medium may be formulated for eliminating wrinkles, frown lines, scarring and other skin conditions instead of using silicone or other products to do so. The conditioned medium contains growth factors and inflammatory mediators such as, for example, VEGF, HGF, IL-6, IL-8, G-CSF and TFG$\beta$, (See Table 3, in Section 5.8.1) as well as extracellular matrix proteins such as type I and type III collagens, fibronectin, tenascin, glycosaminologycans, acid and basic FGF, TGF-$\alpha$ and TGF-$\beta$, KGF, versican, decorin betaglycens, syndean and various other secreted human dermal matrix proteins which are useful in repairing physical anomalies and cosmetic defects. As detailed in section 6.3, Applicants note the effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium. The conditioned medium of the invention significantly increased collagen deposition of tissue in vitro as shown in FIG. 4. The effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium. Of course, the cells used to condition the medium may be genetically engineered to express improved concentrations of such proteins in the medium.

The conditioned media of the invention can be formulated into injectable preparations. Alternatively, products derived from the conditioned media can be formulated. For example, biologically active substances, such as proteins and drugs, can be incorporated in the compositions of the present invention for release or controlled release of these active substances after injection of the composition. Exemplary biologically active substances can include tissue growth factors, such as TGF-, and the like which promote healing and tissue repair at the site of the injection. Methods of product purification include, but are not limited to gel chromatography using matrices such as SEPHADEX®, ion exchange, metal chelate affinity chromatography, with an insoluble matrix such as cross-linked agarose, HPLC purification, hydrophobic interaction chromatography of the conditioned media. Such techniques are described in greater detail in *Cell & Tissue Culture; Laboratory Procedures*, supra; Sanbrook et al., 1989, *Molecular Cloning: A Laboratory Manual*, 2nd Ed., Cold Spring Harbor Lab Press, Cold Spring Harbor, N.Y.

In the injectable embodiment, an aqueous suspension is used and the formulation of the aqueous suspension will typically have a physiological pH (i.e., about pH 6.8 to 7.5). Additionally, a local anesthetic, such as lidocaine, (usually at a concentration of about 0.3% by weight) is usually added to reduce local pain upon injection. The final formulation will also typically contain a fluid lubricant, such as maltose, which must be tolerated by the body. Exemplary lubricant components include glycerol, glycogen, maltose and the like. Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. The final formulation is by definition the processed conditioned cell media in a pharmaceutically acceptable carrier.

The processed conditioned medium is subsequently placed in a syringe or other injection apparatus for precise placement of the conditioned medium at the site of the tissue defect. In the case of formulations for dermal augmentation, the term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200µ I.D.) or even 30 gauge (150µ I.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be more complex.

The above described steps in the process for preparing injectable secreted human conditioned medium are preferably carried out under sterile conditions using sterile materials. The processed conditioned medium in a pharmaceutically acceptable carrier can be injected intradermally or subcutaneously to augment soft tissue, to repair or correct congenital anomalies, acquired defects or cosmetic defects. Examples of such conditions are congenital anomalies as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post-traumatic, post-surgical, post-infectious) such as depressed scars, subcutaneous atrophy (e.g., secondary to discoid lupis erythematosus), keratotic lesions, enophthalmos in the unucleated eye (also superior sulcus syndrome), acne pitting of the face, linear scleroderma with subcutaneous atrophy, saddle-nose deformity, Romberg's disease and unilateral vocal cord paralysis; and cosmetic defects such as glabellar frown lines, deep nasolabial creases, circumoral geographical wrinkles, sunken cheeks and mammary hypoplasia. The compositions of the present invention can also be injected into internal tissues, such as the tissues defining body sphincters to augment such tissues.

Other tissue types used to condition the media include but are not limited to bone marrow, skin, epithelial cells, and cartilage, however, it is expressly understood that the three-dimensional culture system can be used with other types of cells and tissues.

Alternatively, the conditioned cell medium of the present invention may be formulated with polymerizable or cross-linking hydrogels as described in the previous section on wound treatment.

Food Additives and Dietary Supplements

The conditioned media may be used as food additives and formulated into dietary supplements. The conditioned media of the invention contains many useful nutrients including essential amino acids, minerals, and vitamins in an abundance and variety not found in individual foods or good groups. Applicants are unaware of a more balanced food item (other than breast milk) containing such an extensive array of nutrients although such attempts are made in specially formulated, expensive liquid formulas available for both adults and babies. The conditioned cell media and/or products derived thereof, can be used as an inexpensive source for a balanced nutritional supplement for weight loss or alternatively for enhancing the nutritional content of food, particularly for third world countries. The medium is sterile and is free from contamination by human pathogens (i.e., aseptic). The conditioned medium may be concentrated and/or lyophilized and preferably administered in capsules or tablets for ingestion. Alternatively, the compositions may be directly added to adult or baby food to enhance nutritional content. This rich source of nutrients may be processed relatively inexpensively and can be invaluable to undernourished elderly people, and in particular, to children in underdeveloped countries where increased mortality due to poor responses to infection have been associated with malnutrition.

Additionally, many trace elements found in the conditioned media, such as iron and magnesium, are critical for mammalian survival and reproduction, and there is concern that marginal trace element deficiency may be a public health problem. The intake of various essential micronutrients has been suggested to decrease infection as well as cancer risk by modifying specific phases of carcinogenesis. Micronutrients also enhance the functional activities of the immune system and its interacting mechanism of T cells and B cells, Mos, and NK cells specifically by enhancing the production of various cytokines to facilitate their phagocytic and cytotoxic action against invading pathogens and/or to destroy emerging premalignant cells in various vital organs. See, Chandra, R. K. ed. (1988), *Nutrition and Immunology. Contemporary Issues in Clinical Nutrition*, Alan R. Liss, New York. Thus, there is a need for a relatively inexpensive source of balanced nutrients. Ideal food products for enrichment with the conditioned media are breads, cereals and other grain products such as pastas, crackers, etc. Also, the medium may be further processed to concentrate or reduce one or more factor or component contained within the medium, for example, enrichment of a growth factor using immunoaffinity chromatography or, conversely, removal of a less desirable component, for any given application as described in this section.

Animal Feed Supplement

The compositions may be used as a supplemental to animal feed. In one embodiment, the conditioned medium contains bovine serum that provides a source of protein and other factors that are beneficial for mammals such as cattle and other ruminant animals, such as cows, deer and the like. The medium is screened for pathogens and is free of bovine pathogens and mycoplasma. The conditioned medium of the invention is preferably obtained from cows raised in the United States so that the likelihood of pathogens is markedly diminished.

Cell Culture Medium

The medium compositions may be "re-used" to culture cells, particularly cells that are difficult to culture in vitro. Conventional growth medium is typically supplemented with many of the factors already present in Applicants' conditioned medium. Further, the conditioned medium also contains factors that promote cell attachment and growth such as extracellular matrix proteins described above. Increasing fibronectin or collagen concentrations may be beneficial for promoting cell attachment to a scaffold or culture surface. Rather than add these factors to the medium, conditioned medium may be used for culturing cells and preparing three-dimensional tissue constructs, such as Dermagraft®. Applicants have demonstrated that the conditioned medium increases cell proliferation of fibroblasts and keratinocytes, see FIG. 3. Cellular debris or other particulate matter as well as proteases, lactic acid and other components possibly detrimental to cell growth can be removed from the medium prior to its reuse as a cell culture medium. It may also be desirous to use serum in the conditioned cell medium for this application. Serum also contains attachment factors such as fibronectin and serum-spreading factor which promote cell attachment to the substrate. Such attachment is required for the growth of some, but not all, cells in vitro. In addition to providing substances necessary for cell growth, serum may also play a role in stabilizing and detoxifying the culture environment. For example, serum has a significant buffering capacity and contains specific protease inhibitors, such as α1, -antitrypsin and α$_2$-macro globulin. Serum albumin, present in high levels in medium containing, for example, 10% serum, may act as a nonspecific inhibitor of proteolysis as well as bind fat-soluble vitamins and steroid hormones which can be toxic in their free forms. Serum components may also bind and detoxify heavy metals and reactive organics which may be present in the medium components.

Pharmaceutical Applications

The conditioned medium of the invention contain a variety of useful pharmaceutical factors and components such as growth factors, regulatory factors, peptide hormones, antibodies, etc., as described throughout the specification and are therefore useful for a variety of pharmaceutical applications. Also, products which may be added include, but are not limited to, antibiotics, antivirals, antifungals, steroids, analgesics, antitumor drugs, investigational drugs or any compounds which would result in a complimentary or synergistic combination with the factors in the conditioned media. As previously discussed, the cells are cultured, and the media recovered under aseptic conditions. Additionally, the media can be tested for pathogens. If sterilization is done, it must be done in a manner which minimally affects the desired biological activity as described, supra. The medium may be further processed to concentrate or reduce one or more factor or component contained within the medium, for example, enrichment of a growth factor using immunoaffinity chromatography or, conversely, removal of a less desirable component, for any given application as described therein. In a preferred embodiment, formulations are made from medium conditioned by a three-dimensional cell construct. The three-dimensional cultures produce a multitude of growth factors and proteins that are secreted into the medium at optimal physiological ratios and concentrations. See for example, Table 2 in section 5.8.1. The medium, therefore, provides a unique combination of factors and specified ratios that closely represent those found in vivo. Bovine serum is generally not preferred in this application. It may be preferable to remove cellular debris or other particular matter as well as proteases, lactic acid and other components possibly detrimental to cell growth.

The conditioned media may be formulated into pharmaceuticals in the form of tablets, capsules, skin patches, inhalers, eye drops, nose drops, ear drops, suppositories, creams, ointments, injectables, hydrogels and into any other appropriate formulation known to one of skill in the art. For oral administration the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolae); or wetting agents (e.g., sodium lauryl sulphate). Tablets may be coated using methods well known in the art. Liquid preparations for oral administration may take the form of, for example, solutions, syrups or suspensions, or they may be presented as a dry product for constitution with water or other suitable vehicle before use.

Such liquid preparations may be prepared by conventional means with pharmaceutically acceptable additives such as suspending agents (e.g., sorbitol syrup cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The pharmaceutical formulations of the invention may be delivered to a patient via a variety of routes using standard procedures well known to those of skill in the art. For example, such delivery may be site-specific, oral, nasal, intravenous, subcutaneous, intradermal, transdermal, intramuscular or intraperitoneal administration. Also, they may be formulated to function as controlled, slow release vehicles.

Therapeutic products contained in the conditioned media include, but are not limited to, enzymes, hormones, cytokines, antigens, antibodies, clotting factors, and regulatory proteins. Therapeutic proteins include, but are not limited to, inflammatory mediators, angiogenic factors, Factor VIII, Factor IX, erythropoietin (EPO), alpha-1I antitrypsin, calcitonin, glucocerebrosidase, human growth hormone and derivatives, low density lipoprotein (LDL), and apolipoprotein E, IL-2 receptor and its antagonists, insulin, globin, immunoglobulins, catalytic antibodies, the interleukins (ILs), insulin-like growth factors, superoxide dismutase, immune responder modifiers, BMPs (bone morphogenic proteins) parathyroid hormone and interferon, nerve growth factors, tissue plasminogen activators, and colony stimulating factors (CSFs). Of course, the medium may be further processed to concentrate or reduce one or more factor or component contained within the medium, for example, enrichment of a growth factor using immunoaffinity chromatography or, conversely, removal of a less desirable component, for any given application as described herein.

Assays commonly employed by those of skill in the art may be utilized to test the activity of the particular factor or factors, thereby ensuring that an acceptable level of biological activity (e.g., a therapeutically effective activity) is retained by the attached molecule or encapsulated molecule.

Thus, the condition cell media, and products derived from the media of the invention may be used, for example, to provide insulin in the treatment of diabetes, nerve growth factor for the treatment of Alzheimer's disease, factor VIII and other clotting factors for the treatment of hemophilia, dopamine for the treatment of Parkinson's disease, enkaphalins via adrenal chromaffin cells for the treatment of chronic pain, dystrophin for the treatment of muscular dystrophy, and human growth hormone for the treatment of abnormal growth.

Doses of such therapeutic protein agents are well known to those of skill in the art and may be found in pharmaceutical compedia such as the PHYSICIANS DESK REFERENCE, Medical Economics Data Publishers; REMINGTON'S PHARMACEUTICAL SCIENCES, Mack Publishing Co.; GOODMAN & GILMAN, THE PHARMACOLOGICAL BASIS OF THERAPEUTICS, McGraw Hill Publ., THE CHEMOTHERAPY SOURCE BOOK, Williams and Wilkens Publishers.

The therapeutically effective doses of any of the drugs or agents described above may routinely be determined using techniques well known to those of skill in the art. A "therapeutically effective" dose refers to that amount of the compound sufficient to result in amelioration of at least one symptom of the processes and/or diseases being treated.

Toxicity and therapeutic efficacy of the drugs can be determined by standard pharmaceutical procedures in cell cultures or experimental animals, e.g., for determining the LD 50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Additionally, the cells and tissues may be genetically engineered to enhance expression of a desired product such as insulin, for example, and/or to express nucleotide sequences and/or moieties which target the gene products listed above e.g. ribozyme, antisense molecules and triple helices, which may have an inhibitory effect on target gene expression and/or activity. This might be advantageous when culturing tissues in which specialized stromal cells in the medium may play particular structural/functional roles, e.g., glial cells of neurological tissue, Kupffer cells of liver, etc.

Stimulation of Hair Growth

The medium may be conditioned using, for example, human hair papilla cells. Preferably, the medium conditioned by such cells is grown in three-dimensions. Hair papilla cells are a type of mesenchymal stem cell that plays a pivotal role in hair formation, growth and restoration (Matsuzaki et al., *Wound Repair Regen,* 6:524-530 (1998)). The conditioned medium is preferably concentrated and applied as a topical formulation. The conditioned media compositions may be formulated for topical applications using an agent that facilitates penetration of the compound into the skin, for example, DMSO, and applied as a topical application for stimulating hair growth.

The compositions of the invention promote or restore hair growth when applied topically by providing growth factors and other factors that increase epithelial cell migration to hair follicles. In addition to the growth factors found in the conditioned media, other compounds, such as minoxidil and antibiotics can be used. During hair growth there is a reduction in blood supply during catagen (the transitional phase of the hair follicle between growth and resting phases) and telogen (the resting phase). Biologically active molecules derived from the conditioned cell medium can be determined and optimized for use during these phases of hair growth using assays known in the art including the stumptailed macaque model for male-patterned baldness, see for example, Brigham, P. a., A. Cappas, and H. Uno, The Stumptailed Macaque as a Model for Androgenetic Alopecia: Effects of Topical Minoxidil Analyzed by Use of the Folliculogram, *Clin Dermatol,* 1988, 6(4): p. 177-87; Diani, A. R. and C. J. Mills, Immunocytochemical Localization of Androgen Receptors in the Scalp of the Stumptail Macaque Monkey, a Model of Androgenetic Alopecia, *J. Invest Dermatol,* 1994, 102(4): p. 511-4; Holland, J. M., Animal Models of Alopecia, *Clin Dermatol,* 1988, 6(4): p. 159-162; Pan, H. J., et al., Evaluation of RU58841 as an Anti-Androgen in Prostate PC3 Cells and a Topical Anti-Alopecia Agent in the Bald Scalp of Stumptailed Macaques, *Endocrine,* 1998, 9(1): p. 39-43; Rittmaster, R. S., et al., The Effects of N,N-diethyl-4-methyl-3-oxo-4-aza-5 alpha-androstane-17 beta-carboxamide, a 5 alpha-reductase Inhibitor and Antiandrogen, on the Development of Baldness in the Stumptail Macaque, *J. Clin Endocrinol Metab,* 1987, 65(1): p. 188-93 (each of which is incorporated by reference in its entirety). Additional models include measuring differences in hair follicle proliferation from follicles cultured from bald and hairy areas, a newborn rat model as well as a rat model of alopecia areata, see, Neste, D. V., The Growth of Human hair in Nude Mice, *Dermatol Clin.,* 1996, 14(4): p. 609-17; McElwee, K. J., E. M. Spiers, and R. F. Oliver, In Vivo Depletion of CD8+T Cells Restores Hair Growth in the DEBR Model for Alopecia Areata, *Br J Dermatol,* 1996, 135(2): p. 211-7; Hussein, A. M., Protection Against Cytosine Arabinowide-Induced Alopecia by Minoxidil in a Rat Animal Model, *Int J Dermatol,* 1995, 34(7): p. 470-3; Oliver, R. F., et al., The DEBR Rat Model for Alopecia Areata, *J Invest Dermatol,* 1991, 96(5): p. 978; Michie, H. J., et al., Immunobiological Studies on the Alopecic (DEBER) Rat, *Br J Dermatol,* 1990, 123(5): p. 557-67 (each of which is incorporated by reference in its entirety).

EXAMPLES

Conditioning the Medium

Human dermal fibroblasts were seeded onto the substrate of the apparatus described in the '766 patent and described in detail above in Sections 5.3, 5.4 and 5.6. The substrate is within the casing designed to facilitate three-dimensional tissue growth on its surface and the cells were cultured in a closed system in cultured in high glucose DMEM (10% BCS supplemented with 2 mM L-glutamine and 50 mg/ml ascorbic acid) at 37° C. in a humidified, 5% $CO_2$ atmosphere. After 10 days the cell culture was removed, fresh medium was added. The cells were cultured for an additional 4 days as described above. The resulting conditioned medium, having been exposed to the cell and tissue culture for four days (days 10-14) was then removed from the individual chambers and pooled. The conditioned medium (approximately 5 to 10 liters/pool) was dispensed into 200 ml aliquots and further concentrated 10- to 20-fold using a positive pressure concentration device having a filter with a 10,000 MW cut-off (Amicon, Beverly, Mass.). The resulting 10 to 20 ml of concentrated conditioned medium was dispensed into 1 ml aliquots and frozen at −20° C. for analysis. A 1× concentration of conditioned medium results from 10× conditioned medium added to base medium as a 10% (vol/vol) solution. Likewise, a 1× concentration of "medium" or "serum free medium" results from 10× medium (i.e., base medium) or 10× serum free medium (base medium without serum) added to base medium as a 10% (vol/vol) solution which are then used as controls.

Proliferating Activity of Three-Dimensional-Conditioned Medium

Exposure of Fibroblasts and Keratinocytes to the Conditioned Medium

The conditioned medium of Section 6.I, was examined for the ability to promote the proliferation of human fibroblasts and keratinocytes. Human fibroblasts or human basal keratinocytes were seeded into 96 well plates (5,000 cells/well) and cultured in high glucose DMEM (10% BCS supplemented with 2 mM L-glutamine and IX antibiotic/antimycotic) supplemented with IX final concentration of serum-free-medium, medium, or the three-dimensional conditioned medium as described above in Section 6.1. The cultures were maintained at 37° C. in a humidified, 5% $CO_2$ atmosphere for 3 days.

Cellular Proliferation

Cellular proliferation was measured using a commercially available, fluorescent-based dye assay that measures total nucleic acid content as an estimation of cell proliferation (CyQuant Cell Proliferation Assay Kit, Molecular Probes, Eugene, Or). All assays were performed according to the manufacturer's instructions. Medium was removed by blotting and the cells were lysed using lysis buffer containing the green fluorescent dye, CyQuant GR dye. The dye exhibits strong fluorescence enhancement when bound to cellular nucleic acids and the amount of fluorescence is proportional to the amount of nucleic acid present in the sample. Samples were incubated for 5 minutes in the absence of light and sample fluorescence was determined using a microtiter plate reader with filters appropriate for ~480 nm excitation and ~520 nm emission maxima. The amount of nucleic acid in each sample was calculated by comparing the amount of observed fluorescence in each well against a standard curve, derived using known concentrations of calf thymus DNA as a standard.

As shown in FIG. 3, the cells cultured in the medium containing the conditioned medium resulted in increased cellular proliferation of both fibroblast and keratinocyte cells when compared to the two controls.

Modulation of Collagen Deposition into Tissues by Three-Dimensional Conditioned Medium Wound Healing Applications The effect of three dimensional conditioned medium on the preparation and composition of three-dimensional tissues was examined by measuring the amount of collagen secreted into the extracellular matrix of tissues cultured in the presence of serum-free medium, medium or three dimensional conditioned medium.

Nylon scaffolds were laser-cut into 11 mm×11 mm squares, washed in 0.5M acetic acid, rinsed extensively in FBS, and seeded with 12F clinical fibroblasts at passage 8 (~38,000/cm$^2$). Cultures were grown in 1 ml of DMEM (10% BCS supplemented with 2 mM L-glutamine and 1× antibiotic/antimycotic) supplemented with 1× final concentration of serum-free-medium, medium, or the three-dimensional conditioned medium as described above in Section 6.I with the addition of 50 mg/ml ascorbate at each feeding. Copper sulfate was added to a final concentration of 2.5 ng/ml, and high oxygen (40%, about twice atmospheric) was maintained by regulated gassing of a standard incubator. Cultures (n=3 or greater) were maintained at 37° C. in a humidified, 5% $CO_2$ atmosphere for 10 days. A no ascorbate control was also included.

Collagen Isolation

Collagen was isolated and purified to near homogeneity from three-dimensional tissue cultures grown in the presence of base medium supplemented with a 1× final concentration of serum-free medium, medium or three dimensional conditioned medium described above. The purity of the final samples preparations was estimated by subjecting the purified collagen samples to electrophoresis on gradient SDS-polyacrylamide gels, visualizing the separate protein bands using Coomassie blue, and estimating the amount of collagen-specific alpha-, beta- and gamma-bands compared to total protein (below). Purification methods yielded similar patterns in all samples.

Samples were rinsed in PBS, then sterile water, followed by 2-6 hours in 0.5M acetic acid. The samples were then digested overnight in 1 mg/ml pepsin (Worthington, Inc.) in 0.012N HCI at 4° C. Samples were clarified by centrifugation at 13000 rpm at 4° C. Collagen was precipitated 30-60 minutes at 4° C. after addition of 5 M NaCl to a final concentration of 0.7M. Precipitated collagen was separated by centrifugation at 13000 rpm at 4° C. for 30 to 60 minutes, and was resuspended in 0.012N HCI.

Analysis

Total protein was determined using a commercially available colorimetric assay kit (Pierce, Inc. BCA assay kit) and assays were performed according to the manufacturer's instructions. Bovine skin collagens were used as a standard (InVitrogen, Carlsbad, Calif.; Cohesion Technologies, Inc., Palo Alto, Calif.) for quantifying total protein.

Samples 10 mg) were then subjected to SDS-PAGE analysis with electrophoresis on 3-8% gradient gels. The samples of isolated collagens were then heated to 95° C. in reducing sample buffer. Gels were stained with Coomassie Blue, destained, and computer-scanned for visualization.

As shown in FIG. 4, a statistically significant ($p<0.05$) increase in collagen deposition of about 50% was noted for three-dimensional cultures treated with three dimensional conditioned medium compared to either control. The activity could not be attributable to the presence of medium or serum alone.

Such enhanced deposition of collagen in vivo has a number of applications, including wound healing, the treatment of wrinkles and contour lines that appear with increased age as well as being able to promote matrix deposition over bony-prominences susceptible to pressure ulcers in paralyzed or bedridden patients.

Antioxidant Activity

Exposure of Epidermal Skin Cells to the Conditioned Medium

Antioxidant agents have demonstrated the potential to reverse/prevent cell aging and malignancy. The antioxidant activity of the three-dimensional conditioned medium was measured on human epidermal skin cells. Human basal keratinocytes (~100,000/well) were cultured in Petri dishes in the presence of MCDB153 medium (KGM, Clonetics, Inc.) supplemented with 1× three dimensional conditioned medium, medium or serum-free medium controls for 3 days at 37° C. in a humidified, 5% $CO_2$ atmosphere. The medium was removed from each sample, the cells were isolated from the dish by incubating in the presence of trypsin (Sanbrook et al., 1989, *Molecular Cloning: A Laboratory Manual,* 2nd Ed., Cold Spring Harbor Lab Press, Cold Spring Harbor, N.Y.), followed by centrifugation.

FACS Analysis

The isolated cells were incubated in the presence of 1 mM dihydrorhodamine-1,2,3 (Molecular Probes, Eugene, Or) at 37° C. for 30 minutes and then analyzed by FACS (fluorescence-activated cell sorting) analysis using a Becton-Dickinson (Franklin Lakes, N.J.) FACSCAN apparatus according to the manufacturer's instructions. The amount of intracellular oxidation of the reduced dihydrorhodamine dye is directly proportional to the amount of detectable intracellular fluorescence of the oxidized state of the dye.

Results

Human keratinocytes exposed to Applicants' conditioned cell medium exhibited a statistically significant ($p<0.0003$) 50% reduction in intracellular oxidation compared to the same cells incubated in the presence of serum-free or serum-containing medium (see FIG. 5). The observed difference do not appear to be attributable to serum factors or ascorbic acid that are present in the control samples. Therefore, topical administration of medium conditioned by three-dimensional cultures may be useful as a cosmeceutical useful for treating or reversing the effects of aging cells.

Occlusive Patch Test Assessing the In Vivo Effects of a Bioengineered Cosmeceutical Nutrient Solution of Human Skin Experimental Design Six consenting adult females (30-60 yr) in good health were enrolled. Exclusion criteria included sensitivity to proteins, skin diseases, damaged skin in or near test sites, diabetes, renal, heart or immunological disorders, use of anti-inflammatory, immuno suppressive, antihistamine or topical drugs or cosmetics and pregnancy. Test articles were assigned to test sites (2 sites, 3.8 cm2) on the right or left forearm of each subject according to a rotational scheme to minimize position or order bias. Site 1 obtained vehicle control and site 2 obtained treatment (i.e., conditioned medium). Occlusion patches were of a Webril nonwoven cotton pad with either 0.2 ml of vehicle or treatment. Patches were covered and held by a 3M occlusive, plastic, hypoallergenic tape. Occlusion patches were positioned daily on the forearms of 3 subjects for 5 consecutive, 24-hour periods. The remaining 3 subjects were patched daily for 12, consecutive 24-hour periods (treatment still ongoing). On the day following the last patch application, a 2-mm biopsy is taken from each site. This protocol was approved by the IRB for the investigative organization, the California Skin Research Institute (San Diego, Calif.), and is in accordance with Title 21 of the CFR, Parts 50 and 56.

Evaluations

Gross observations were graded for glazing, peeling, scabbing, fissuring, hyperpigmentation, and hypopigmentation. Irritation was scored visually using a 5 point scale and graded numerically for erythema, edema, papules and vesicles (>25% patch site), and identifiable reactions (<25% patch site), i.e., bulla reaction with or without weeping, spreading, and induration. The H & E histological assessment by a board certified pathologist included parameters for viable epidermal thickness, epidermal hyperplasia (acanthosis), granular cell layer thickness, inflammatory infiltrate, mitotic figures, appearance of collagen and elastic fibers, and vasculature.

Results

No adverse events were induced by the conditioned medium or control in the 3 subjects receiving a 5-day treatment. Averages of the daily irritation scores for the nutrient solution (0.3) and the controls (0.2) indicated both sites frequently showed no visible reaction or erythema or showed slight, confluent or patchy erythema. Histology (trichrome collagen stain) showed healthy tissue for all parameters measured. Hence, the conditioned medium exhibits agreeable affects on human skin.

Modulation of Human Endothelial Cell Behavior

The effects of conditioned medium and human matrix produced by matrix-bound fibroblasts on angiogenesis and endothelial cell motility were determined. Conditioned medium was produced via passage through the three dimensional fibroblast culture described herein (described in Sections 5.3, 5.4 and 5.6) and was either concentrated (10×) or lyophilized. Human extracellular matrix was physically removed from the tissue after production.

Endothelial Cell Tubule Formation Assay

Endothelial cell tubule formation assay with human umbilical vein endothelial cells (HUVEC) was used to assess angiogenesis. Co-culture of HUVEC with lyophilised conditioned medium caused an increase in tubule formation when compared to the negative control (pre-conditioned medium) 4.9±9.31 mm and 0.00±0.00 mm respectively; concentrated medium increased tubule formation to 44.10±1.75 mm; and the human extracellular matrix increased tubule formation to 39.3±5.6 mm Wounding Assay A confluent layer of endothelial cells were scratched and the speed of closure of the resulting "wound" was measured used to assess cell motility. The "wounding" assay was measured as speed of closure in mm/h (millimeters/hour). Endothelial cells treated with lyophilised medium exhibited a speed of 25.59±12.907 mm/h): the concentrated medium a speed of 39.56±15.87 mm/h. Human extracellular matrix showed no increase in speed when compared to the negative control (pre-conditioned medium) 0.00 mm/h and 27.96±10.01 mm/h for human extracellular matrix and negative control respectively.

Thus, as illustrated by changes in angiogenesis (tubule formation assay) and cell motility (assessed using the "wounding" assay) the conditioned medium of the invention is able to modulate the behavior of human endothelial cells.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims. Various publications are cited herein, the disclosures of which are incorporated by reference in their entireties.

What is claimed is:

1. A method for reducing or eliminating a skin wrinkle, the method comprising the step of topical application of a composition comprising:
   (a) a conditioned medium comprising:
      (i) a fibroblast growth factor, a platelet derived growth factor, an epidermal growth factor, vascular endothelial growth factor, a bone morphogenic protein, a transforming growth factor; an insulin like growth factor, and
      (ii) collagen; and
   (b) an acceptable carrier;
   wherein the skin wrinkle is reduced or eliminated by topical application of the composition, and
   wherein the conditioned medium does not contain a dextran and the conditioned medium is made by a process comprising the steps of:
   (a) inoculating not genetically engineered, fresh, not freeze-thaw, human fetal fibroblasts onto a substrate in a nutrient medium;
   (b) culturing the not genetically engineered fresh, not freeze-thaw human, fetal fibroblasts in a two dimensional culture so that the not genetically engineered, fresh, not freeze-thaw human fetal fibroblasts secrete the fibroblast growth factor, platelet derived growth factor, epidermal growth factor, vascular endothelial growth factor, bone morphogenic protein, transforming growth factor and the insulin like growth factor into the nutrient medium, until the nutrient medium becomes a conditioned medium; and
   (c) removing the conditioned medium from the cultured cells,
   wherein the nutrient medium contains bovine calf serum; and
   wherein the composition is stable for up to 2 years in storage at −20° C.

2. The method of claim 1, where the method fortifies the skin.

3. The method of claim 1, wherein the composition is a cream or ointment.

4. The method of claim 1, wherein the conditioned medium comprises keratinocyte growth factor.

5. The method of claim 1 wherein the conditioned medium comprises granulocyte colony-stimulating factor.

6. The method of claim 1, wherein the conditioned medium comprises transforming growth factor-beta.

7. The method of claim 1, wherein the conditioned medium comprises interleukin-6.

* * * * *